(12) United States Patent
Bernardon et al.

(10) Patent No.: US 6,831,106 B1
(45) Date of Patent: Dec. 14, 2004

(54) VITAMIN D ANALOGUES

(75) Inventors: Jean-Michel Bernardon, Nice (FR); Thibaud Biadatti, Opio (FR)

(73) Assignee: Galderma Research & Development, S.N.C., Valbonne (FR)

( * ) Notice: Subject to any disclaimer, the term of this patent is extended or adjusted under 35 U.S.C. 154(b) by 0 days.

(21) Appl. No.: 10/130,941

(22) PCT Filed: Nov. 22, 2000

(86) PCT No.: PCT/FR00/03249

§ 371 (c)(1),
(2), (4) Date: Sep. 5, 2002

(87) PCT Pub. No.: WO01/38303

PCT Pub. Date: May 31, 2001

(30) Foreign Application Priority Data

Nov. 24, 1999 (FR) .............................................. 99 14781

(51) Int. Cl.[7] .................... A61K 31/045; A61K 31/435; A61K 31/38; C07D 207/46; C07D 333/16
(52) U.S. Cl. ...................... 514/730; 514/277; 514/438; 514/461; 514/428; 568/807; 546/344; 549/78; 549/502; 548/570
(58) Field of Search ................................ 514/730, 277, 514/438, 461, 428; 568/807; 546/344; 549/78, 502; 548/570

(56) References Cited

U.S. PATENT DOCUMENTS

| | | | |
|---|---|---|---|
| 6,150,413 A * | 11/2000 | Bernardon et al. ......... 514/568 |
| 6,274,635 B1 * | 8/2001 | Travis ........................ 514/718 |
| 6,288,055 B1 * | 9/2001 | Natarajan et al. ........ 514/210.2 |
| 6,342,642 B1 * | 1/2002 | Hu et al. .................... 568/637 |
| 6,362,371 B1 * | 3/2002 | Moran et al. ............... 564/365 |
| 6,442,367 B1 * | 8/2002 | Itami et al. ................. 399/349 |
| 6,444,709 B1 * | 9/2002 | Diaz et al. ................... 514/706 |
| 6,541,669 B1 * | 4/2003 | Moran et al. ............... 564/372 |
| 6,683,115 B2 * | 1/2004 | Moran et al. ............... 514/655 |

FOREIGN PATENT DOCUMENTS

| | | |
|---|---|---|
| EP | 0 375 368 | 6/1990 |
| EP | 0 661 260 | 7/1995 |
| EP | 0 728 739 | 8/1996 |
| EP | 0 879 814 | 11/1998 |
| EP | 0 947 496 | 10/1999 |
| WO | WO 95/27692 | 10/1995 |
| WO | WO 98/20866 | 5/1998 |

* cited by examiner

*Primary Examiner*—Deborah C. Lambkin
(74) *Attorney, Agent, or Firm*—Burns, Doane, Swecker & Mathis, L.L.P.

(57) ABSTRACT

The present invention relates to novel triaromatic compounds having the general formula (I):

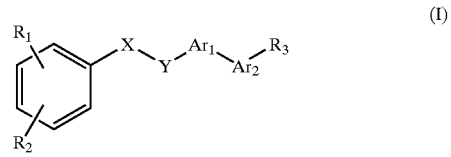

Figure 1:
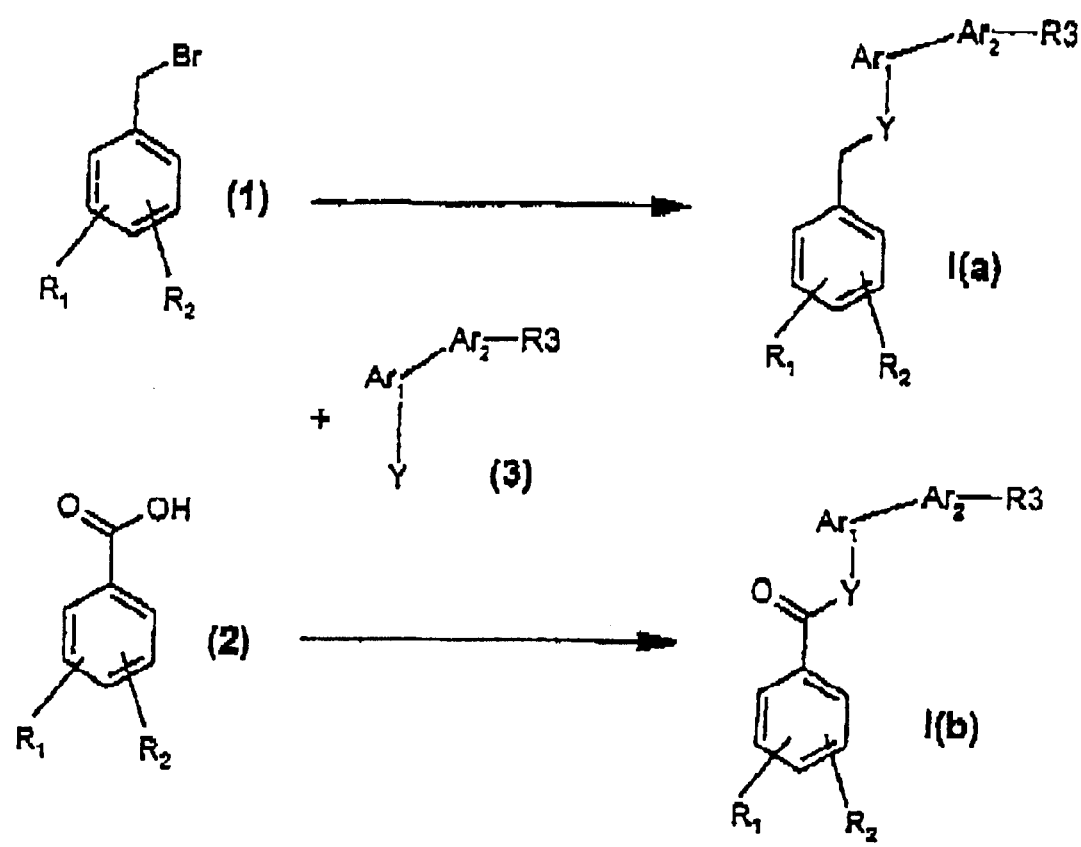

as well as to a method for preparing them and to their use in pharmaceutical compositions intended for use in human or veterinary medicine (in dermatology, in carcinology and in the field of autoimmune diseases and that of organ or tissue transplants in particular), or alternatively in cosmetic compositions.

16 Claims, 6 Drawing Sheets

VITAMIN D ANALOGUES

The invention relates, as novel and useful industrial products, to triaromatic compounds which are vitamin D analogues. The invention also relates to a process for preparing them and to their use in pharmaceutical compositions intended for use in human or veterinary medicine, or alternatively in cosmetic compositions.

The compounds according to the invention have pronounced activity in the fields of cell proliferation and differentiation and find applications more particularly in the topical and systemic treatment of dermatological (or other) complaints associated with a keratinization disorder, complaints with an inflammatory and/or immunoallergic component and hyperproliferation of tissues of ectodermal origin (skin, epithelium, etc.), whether benign or malignant. These compounds can also be used to combat ageing of the skin, whether light-induced or chronological, and to treat cicatrization disorders.

The compounds according to the invention can also be used in cosmetic compositions for body and hair hygiene.

Vitamin D is an essential vitamin for preventing and treating mineralization defects of cartilage (rickets) and of bone (osteomalacia), and even of certain forms of osteoporosis in elderly people. However, it is now accepted that its functions extend well beyond regulating bone metabolism and calcium homeostasis. Among these functions, mention may be made of its actions on cell proliferation and differentiation and the control of the immune defences. Their discovery has opened the way to novel therapeutic approaches in dermatology, carcinology and in the field of autoimmune diseases and that of organ or tissue transplants.

An efficient therapeutic supply has long been confounded by the toxicity of this vitamin (occasionally fatal hypercalcaemia). Structural analogues of vitamin D are currently synthesized, some of which conserve only the differentiating properties and have no action on calcium metabolism.

One of the aims of the present invention is to propose novel compounds which are structural analogues of vitamin D and which show selective activity on cell proliferation and differentiation without displaying any hypercalcaemiant nature.

Another aim of the present invention is to propose novel compounds which are analogues of vitamin D and which are more readily synthesized and thus more economical than those known previously.

Thus, the present invention relates to compounds which can be represented by the general formula (I) below:

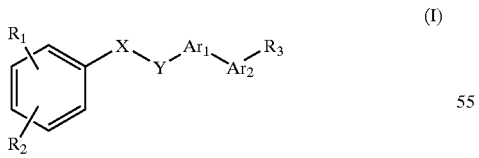

(I)

in which:

$R_1$ represents a hydrogen atom, a $CH_3$ radical or a radical $-(CH_2)_r-OR_4$, $R_2$ represents a radical $-(CH_2)_s-OR_5$ r, s, $R_4$ and $R_5$ having the meanings given below, X—Y represents a bond chosen from the bonds of formulae (a) to (d) below which can be read from left to right or vice-versa:

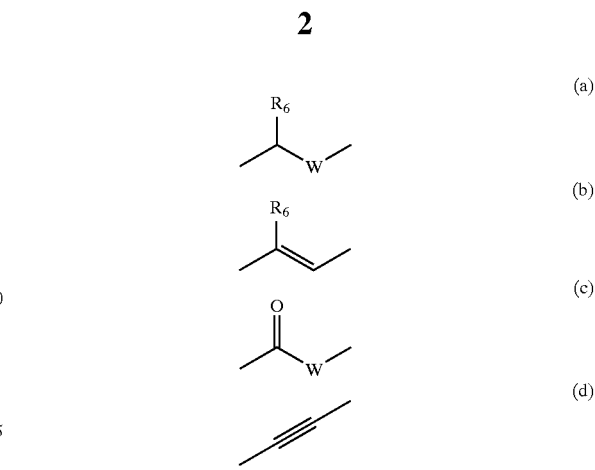

$R_6$ and W having the meanings given below, $Ar_1$ represents a ring of formulae (e) to (i) below:

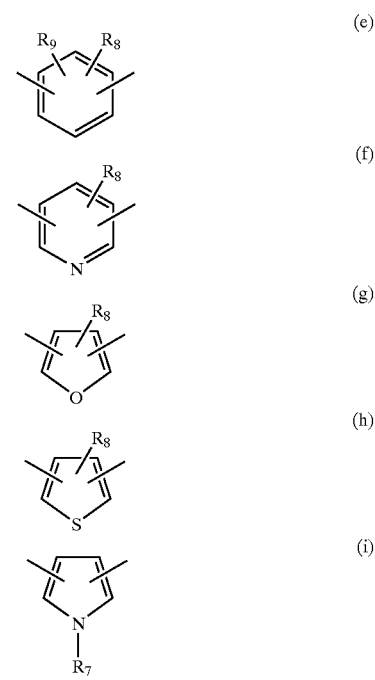

$R_7$, $R_8$ and $R_9$ having the meanings given below, $Ar_2$ represents a ring of formulae (j) to (n) below:

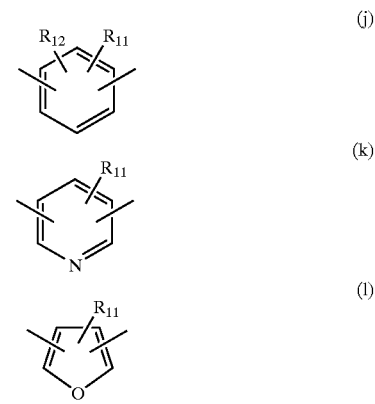

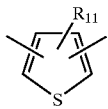
(m)

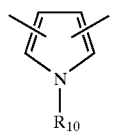
(n)

$R_{10}$, $R_{11}$ and $R_{12}$ having the meanings given below,
$R_3$ represents a radical of formula:

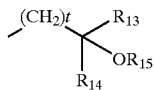

t, $R_{13}$, $R_{14}$ and $R_{15}$ having the meanings given below,
r and s, which may be identical or different, being 1 or 2,
$R_4$ and $R_5$, which may be identical or different, represent a hydrogen atom, an acetyl radical, a benzoyl radical, a trimethylsilyl radical, a tert-butyldimethylsilyl radical or a tetrahydropyranyl radical,
$R_6$ represents a hydrogen atom or a lower alkyl radical,
W represents an oxygen or sulphur atom, a $CH_2$ radical or an NH radical which can be substituted with a lower alkyl radical,
$R_7$ and $R_{10}$, which may be identical or different, represent a hydrogen atom or a lower alkyl radical,
$R_8$, $R_9$, $R_{11}$ and $R_{12}$, which may be identical or different, represent a hydrogen atom, a lower alkyl radical, a halogen atom, a radical —$OR_{16}$, a polyether radical, a $CF_3$ radical, an $NO_2$ radical or an amino radical which may be substituted with one or two lower alkyl radicals, $R_{16}$ having the meanings given below,
t being 0 or 1,
$R_{13}$ and $R_{14}$, which may be identical or different, represent a hydrogen atom, a lower alkyl radical, a cycloalkyl radical, a $CF_3$ radical or a $C_2F_5$ radical,
$R_{15}$ represents a hydrogen atom, an acetyl radical, a trimethylsilyl radical, a tert-butyldimethylsilyl radical or a tetrahydropyranyl radical,
$R_{16}$ represents a hydrogen atom or a lower alkyl radical.

The invention is also directed towards the optical and geometrical isomers of the said compounds of formula (I) as well as to the salts thereof when X—Y represent a bond of formula (a) and W represents an —NH— radical optionally substituted with a lower alkyl radical.

When the compounds according to the invention are in the form of salts, they are pharmaceutically or cosmetically acceptable salts obtained by addition of an inorganic or organic acid, in particular hydrochloric acid, sulphuric acid, acetic acid, fumaric acid, hemisuccinic acid, maleic acid or mandelic acid.

According to the present invention, the expression "lower alkyl radical" means a linear or branched radical containing from 1 to 6 carbon atoms, and preferably methyl, ethyl, isopropyl, tert-butyl and hexyl radicals.

The expression "cycloalkyl radical" means a cyclic alkane radical containing from 3 to 6 carbon atoms. The cycloalkyl radical is preferably chosen from a cyclopropyl, cyclopentyl or cyclohexyl radical.

The expression "halogen atom" preferably means a fluorine, chlorine or bromine atom.

The expression "polyether radical" means a radical containing from 2 to 5 carbon atoms interrupted with at least two oxygen atoms, such as methoxymethoxy, methoxyethoxy and methoxyethoxymethoxy radicals.

Among the compounds of formula (I) falling within the context of the present invention, mention may be made in particular of the following:

{5-[4'-(1-ethyl-1-hydroxypropyl)biphenyl-3-yloxymethyl]-2-hydroxymethylphenyl}methanol {2-hydroxymethyl-5-[4'-(1-hydroxy-1-methylethyl)biphenyl-3-yloxymethyl]phenyl}methanol {5-[4'-(1-ethyl-1-hydroxypropyl)-2'-methylbiphenyl-3-yloxymethyl]-2-hydroxymethylphenyl}methanol {2-hydroxymethyl-5-[4'-(1-hydroxy-1-methylethyl)-2'-methylbiphenyl-3-yloxymethyl]phenyl}methanol (5-{2-[3'-(1-ethyl-1-hydroxypropyl)biphenyl-3-yl]ethyl})-2-hydroxymethylphenyl}methanol {2-hydroxymethyl-5-[3'-(1-hydroxy-1-methylethyl)biphenyl-3-yloxymethyl]phenyl}methanol {5-[4'-(2-ethyl-2-hydroxybutyl)biphenyl-3-yloxymethyl]-2-hydroxymethylphenyl}methanol {5-[3'-(2-ethyl-2-hydroxybutyl)biphenyl-3-yloxymethyl]-2-hydroxymethylphenyl}methanol 1-[3'-(3,4-bis-hydroxymethyl-benzyloxy)biphenyl-3-yl]-2-methyl-2-propanol {4-[4'-(1-ethyl-1-hydroxypropyl)-2'-methylbiphenyl-3-ylsulphanylmethyl]-2-hydroxymethylphenyl}methanol {4-[4'-(1-ethyl-1-hydroxypropyl)-2,2-dimethylbiphenyl-3-yloxymethyl]-2-hydroxymethylphenyl}methanol {2-hydroxymethyl-4-[4'-(1-hydroxy-1-propylbutyl)-2,2-dimethylbiphenyl-3-yloxymethyl]phenyl}methanol {4-[4'-(1-ethyl-1-hydroxypropyl)-2-methylbiphenyl-3-yloxymethyl]-2-hydroxymethylphenyl}methanol {4-[4'-(1-ethyl-1-hydroxypropyl)-2,2',6'-trimethylbiphenyl-3-yloxymethyl]-2-hydroxymethyl-phenyl}methanol (4-{3-[5-(1-ethyl-1-hydroxypropyl)-2-pyridyl]phenoxymethyl}-2-hydroxymethylphenyl)methanol {4-[4'-(1-ethyl-1-hydroxypropyl)-6,2'-dimethylbiphenyl-3-yloxymethyl]-2-hydroxymethylphenyl}methanol {4-[4'-(1-ethyl-1-hydroxypropyl)-6,2',6'-trimethylbiphenyl-3-yloxymethyl]-2-hydroxymethyl-phenyl}methanol {4-[4'-(1-ethyl-1-hydroxypropyl)-6-methylbiphenyl-3-yloxymethyl]-2-hydroxymethylphenyl}methanol {4-[4'-(1-ethyl-1-hydroxypropyl)-2',6'-dimethylbiphenyl-3-yloxymethyl]-2-hydroxymethylphenyl}methanol 1-{4-[3-(3,4-bis-hydroxymethyl-benzyloxy)phenyl]-2-thienyl}-1-propanol (4-{3-[4-(1-ethyl-1-hydroxypropyl)-2-thienyl]phenoxymethyl}-2-hydroxymethylphenyl)methanol {4-[4'-(1-ethyl-1-hydroxypropyl)-2'-methylbiphenyl-3-ylmethoxy]-2-hydroxymethylphenyl}methanol 1-[3'-(3,4-bis-hydroxymethyl-phenoxymethyl)-2-methylbiphenyl-4-yl]-1-propanol {4-[4'-(1-ethyl-1-hydroxypropyl)-3'-methylbiphenyl-3-yloxymethyl]-2-hydroxymethylphenyl}methanol {5-[4'-(1-ethyl-1-hydroxypropyl)-2'-methylbiphenyl-4-yloxymethyl]-2-hydroxymethylphenyl}methanol {4-[2'-tert-butyl-4'-(1-ethyl-1-hydroxypropyl)biphenyl-3-yloxymethyl]-2-hydroxymethylphenyl}methanol 1-[3'-(3,4-bis-hydroxymethyl-benzyloxy)-2-methylbiphenyl-4-yl[-2,2-dimethyl-1-propanol 1-[3'-(3,4-bis-hydroxymethyl-benzyloxy)-2-methylbiphenyl-4-yl]-2-methyl-1-propanol {2-hydroxymethyl-4-[methyl(trifluorohydroxytrifluoromethylethyl)biphenyl-3-yloxymethyl]phenyl}methanol

[5-(2-{5-[4-(1-ethyl-1-hydroxypropyl)-2-methylphenyl]-2-thienyl}ethyl)-2-hydroxymethylphenyl)methanol (5-{5'-[4-(1-ethyl-1-hydroxypropyl)-2-methylphenyl]-2-thienylmethoxy}-2-hydroxymethylphenyl)methanol

[5-(2-{5-[2-ethyl-4-(1-ethyl-1-hydroxypropyl)phenyl]-2-thienyl}ethyl)-2-hydroxymethylphenyl]methanol (5-{5-[2-ethyl-4-(1-ethyl-1-hydroxypropyl)phenyl]-2-thienylmethoxy}-2-hydroxymethylphenyl)methanol

[5-(2-{5-[4-(1-ethyl-1-hydroxypropyl)-2-methylphenyl]-4-methyl-2-thienyl}ethyl)-2-hydroxymethylphenyl]-methanol (5-{5-[4-(1-ethyl-1-hydroxypropyl)-2-methylphenyl]-4-methyl-2-thienylmethoxy}-2-hydroxymethylphenyl)methanol

[2-hydroxymethyl-5-{2-[5-[methyl(trifluorohydroxytrifluoromethylethyl)phenyl]-2-thienyl}ethyl)phenyl]-methanol (2-hydroxymethyl-5-{5-[methyl(trifluorohydroxytrifluoromethylethyl)phenyl]-2-thienylmethoxy}phenyl)-methanol

[5-(2-{5-[ethyl(trifluorohydroxytrifluoromethylethyl)-phenyl]-2-thienyl}ethyl)-2-hydroxymethylphenyl]methanol (5-{5-[ethyl(trifluorohydroxytrifluoromethylethyl)-phenyl]-2-thienylmethoxy}-2-hydroxymethylphenyl)-methanol

[2-hydroxymethyl-5-(2-{methyl[methyl(trifluorohydroxytrifluoromethylethyl)phenyl]-2-thienyl}ethyl)phenyl]-methanol {2-hydroxymethyl-5-(methyl[methyl(trifluorohydroxytrifluoromethylethyl)phenyl]-2-thienylmethoxy}phenyl)-methanol

[5-(2-{5-[4-(1-ethyl-1-hydroxypropyl)-2-methylphenyl]-3-thienyl}ethyl)-2-hydroxymethylphenyl]methanol (5-{5-[4-(1-ethyl-1-hydroxypropyl)-2-methylphenyl]-3-thienylmethoxy}-2-hydroxymethylphenyl)methanol

[5-(2-{5-[2-ethyl-4-(1-ethyl-1-hydroxypropyl)phenyl]-3-thienyl}ethyl)-2-hydroxymethylphenyl]methanol (5-{5-[2-ethyl-4-(1-ethyl-1-hydroxypropyl)phenyl]-3-thienylmethoxy}-2-hydroxymethylphenyl)methanol

[2-hydroxymethyl-5-(2-{5-[methyl(trifluorohydroxytrifluoromethylethyl)phenyl]-3-thienyl}ethyl)phenyl]-methanol (2-hydroxymethyl-5-{5-[methyl(trifluorohydroxytrifluoromethylethyl)phenyl]-3-thienylmethoxy}phenyl)-methanol

[5-(2-{5-[ethyl(trifluorohydroxytrifluoromethylethyl)-phenyl]-3-thienyl}ethyl)-2-hydroxymethylphenyl]methanol (5-{5-[ethyl(trifluorohydroxytrifluoromethylethyl)-phenyl]-3-thienylmethoxy}-2-hydroxymethylphenyl)-methanol

[5-(2-{4-[4-(1-ethyl-1-hydroxypropyl)-2-methylphenyl]-2-thienyl}ethyl)-2-hydroxymethylphenyl]methanol (5-{4-[4-(1-ethyl-1-hydroxypropyl)-2-methylphenyl]-2-thienylmethoxy}-2-hydroxymethylphenyl)methanol

[5-(2-{4-[2-ethyl4-(1-ethyl-1-hydroxypropyl)phenyl]-2-thienyl}ethyl)-2-hydroxymethylphenyl]methanol (5-{4-[2-ethyl-4-(1-ethyl-1-hydroxypropyl)phenyl]-2-thienylmethoxy}-2-hydroxymethylphenyl)methanol

[5-(2-{4-[4-(1-ethyl-1-hydroxypropyl)-2-methylphenyl]-5-methyl-2-thienyl}-ethyl)-2-hydroxymethylphenyl]-methanol (5-{4-[4-(1-ethyl-1-hydroxypropyl)-2-methylphenyl]-5-methyl-2-thienylmethoxy}-2-hydroxymethylphenyl)methanol

[2-hydroxymethyl-5-(2-{4-[methyl(trifluorohydroxytrifluoromethylethyl)phenyl]-2-thienyl}ethyl)phenyl]-methanol (2-hydroxymethyl-5-{4-[methyl(trifluorohydroxytrifluoromethylethyl)phenyl]-2-thienylmethoxy}phenyl]-methanol

[5-(2-(4-[ethyl(trifluorohydroxytrifluoromethylethyl)-phenyl]-2-thienyl}ethyl)-2-hydroxymethylphenyl]methanol (5-{4-[ethyl(trifluorohydroxytrifluoromethylethyl)-phenyl]-2-thienylmethoxy}-2-hydroxymethylphenyl)-methanol

[2-hydroxymethyl-5-(2-{methyl[methyl(trifluorohydroxytrifluoromethylethyl)phenyl]-2-thienyl}ethyl)phenyl]-methanol (2-hydroxymethyl-5-{methyl[methyl(trifluorohydroxytrifluoromethylethyl)phenyl]-2-thienylmethoxy}phenyl)-methanol {5-[2'-ethyl-4'-(1-ethyl-1-hydroxypropyl)-6-methylbiphenyl-3-yloxymethyl]-2-hydroxymethylphenyl}-methanol {5-[4'-(1-ethyl-1-hydroxypropyl)-2'-isopropyl-6-methylbiphenyl-3-yloxymethyl]-2-hydroxymethylphenyl}-methanol {5-[2'-tert-butyl-4'-(1-ethyl-1-hydroxypropyl)-6-methylbiphenyl-3-yloxymethyl]-2-hydroxymethylphenyl}-methanol {5-[ethylmethyl(trifluorohydroxytrifluoromethylethyl)-biphenyl-3-yloxymethyl]-2-hydroxymethylphenyl}methanol {2-hydroxymethyl-5-[2'-isopropyl-6-methyl-4'-(2,2,2-trifluoro-1-hydroxy-1-trifluoromethylethyl)biphenyl-3-yloxymethyl]phenyl}methanol {5-[dimethylethylmethyl(trifluorohydroxytrifluoromethylethyl)biphenyl-3-yloxymethyl]-2-hydroxymethylphenyl}methanol {5-[6-ethyl-4'-(1-ethyl-1-hydroxypropyl)-2'-methylbiphenyl-3-yloxymethyl]-2-hydroxymethylphenyl}methanol {5-[4'-(1-ethyl-1-hydroxypropyl)-6-methoxy-2'-methylbiphenyl-3-yloxymethyl]-2-hydroxymethylphenyl}methanol {5-[6-tert-butyl-4'-(1-ethyl-1-hydroxypropyl)-2'-methylbiphenyl-3-yloxymethyl]-2-hydroxymethylphenyl}-methanol {5-[ethylmethyl(trifluorohydroxytrifluoromethylethyl)-biphenyl-3-yloxymethyl]-2-hydroxymethylphenyl}methanol {2-hydroxymethyl-5-[6-methoxy-2'-methyl-4'-(2,2,2-trifluoro-1-hydroxy-1-trifluoromethylethyl)biphenyl-3-yloxymethyl]phenyl}methanol {5-[dimethylethylmethyl(trifluorohydroxytrifluoromethylethyl)biphenyl-3-yloxymethyl]-2-hydroxymethyl-phenyl}methanol (5-{2-[4'-(1-ethyl-1-hydroxypropyl)-6,2'-dimethylbiphenyl-3-yl]ethyl}-2-hydroxymethylphenyl)-methanol (5-{2-[dimethyl(trifluorohydroxytrifluoromethylethyl)-biphenyl-3-yl]ethyl}-2-hydroxymethylphenyl)methanol (5-{[4'-(1-ethyl-1-hydroxypropyl)-6,2'-dimethylbiphenyl-3-ylamino]methyl}-2-hydroxymethyl-phenyl)methanol (5-{[dimethyl(trifluorohydroxytrifluoromethylethyl)-biphenyl-3-ylamino]methyl}-2-hydroxymethylphenyl)-methanol

[5-({[4'-(1-ethyl-1-hydroxypropyl)-6,2'-dimethylbiphenyl-3-yl]methylamino}methyl)-2-hydroxymethylphenyl]-methanol

[5-({[dimethyl(trifluorohydroxytrifluoromethylethyl)-biphenyl-3-yl]methylamino}methyl)-2-hydroxymethyl-phenyl]methanol According to the present invention, the compounds of formula (I) which are more particularly preferred are those for which at least one, and preferably all, of the conditions below are satisfied:

$R_1$ represents a $CH_3$ or $CH_2OH$ radical,
$R_2$ represents a $CH_2OH$ radical,
X—Y represents a bond of formula (a) or (c),
$R_3$ represents the radical $C(R_{13})(R_{14})OH$.

A subject of the present invention is also processes for preparing the compounds of formula (I).

FIGS. 1 to 5 represent reaction schemes which can be used to prepare the compounds according to the invention.

Thus, the compounds of formula I(a) can be obtained (FIG. 1) by reacting a halo compound, preferably a bromo compound (1) with a phenolic (Y=OH), thiophenolic (Y=SH) or aniline (Y=NH—COO-tert-butyl) derivative (3) in the presence of a base such as $K_2CO_3$ in a solvent such as acetone or methyl ethyl ketone.

The compounds of formula I(a) can also be obtained (FIG. 1) by reacting a halo compound, preferably a bromo compound (1) with the sodium or potassium salt of a phenolic (Y=OH), thiophenolic (Y=SH) or aniline (Y=NH—COO-tert-butyl) derivative (3) in a solvent such as dimethylformamide (DMF).

The compounds of formula I(b) can be obtained (FIG. 1) by reacting a benzoic derivative (2) with a phenolic (Y=OH), thiophenolic (Y=SH) or aniline (Y=NH$_2$) derivative (3) in the presence of carbonyldiimidazole or dicyclohexylcarbodiimide in a solvent such as dichloromethane or tetrahydrofuran (THF).

The compounds of formula I(b) can also be obtained (FIG. 1) by reacting a benzoyl chloride (obtained by reacting a benzoic derivative (2) with thionyl chloride or oxalyl chloride) with a phenolic (Y=OH), thiophenolic (Y=SH) or aniline (Y=NH$_2$) derivative (3) in the presence of a base such as triethylamine in a solvent such as dichloromethane or tetrahydrofuran (THF).

Figure 2:
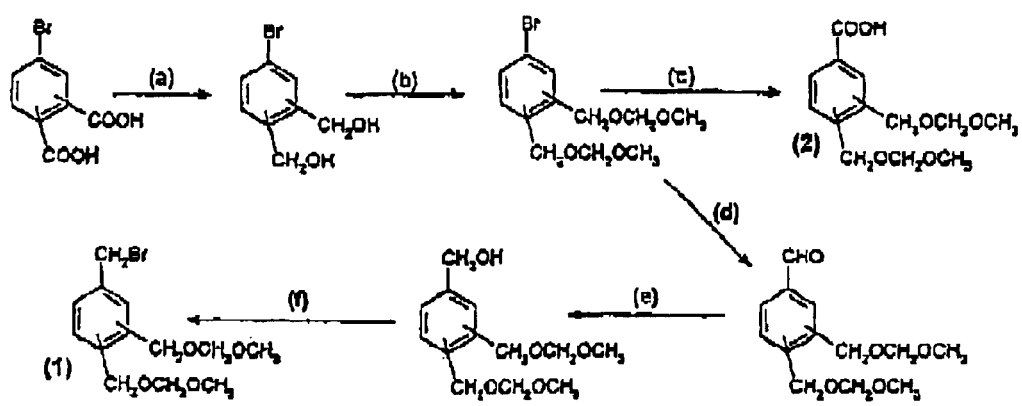
Figure 3:
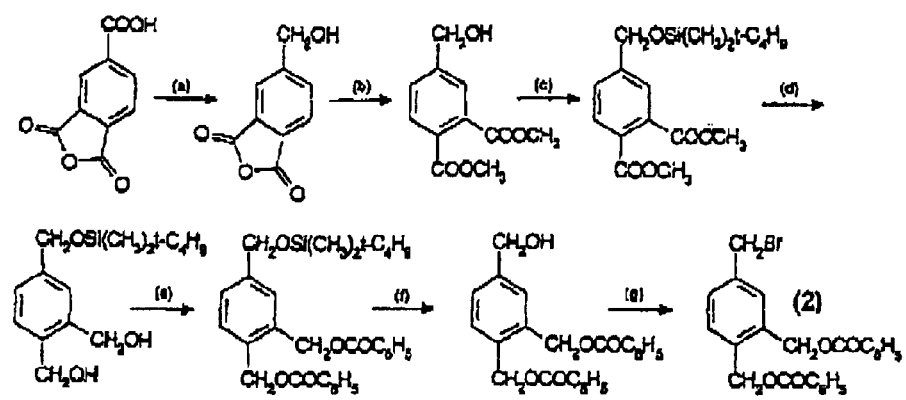
Figure 4:
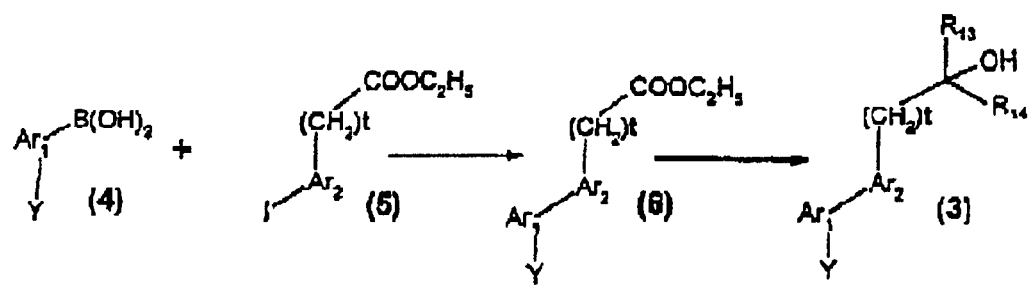
Figure 5:
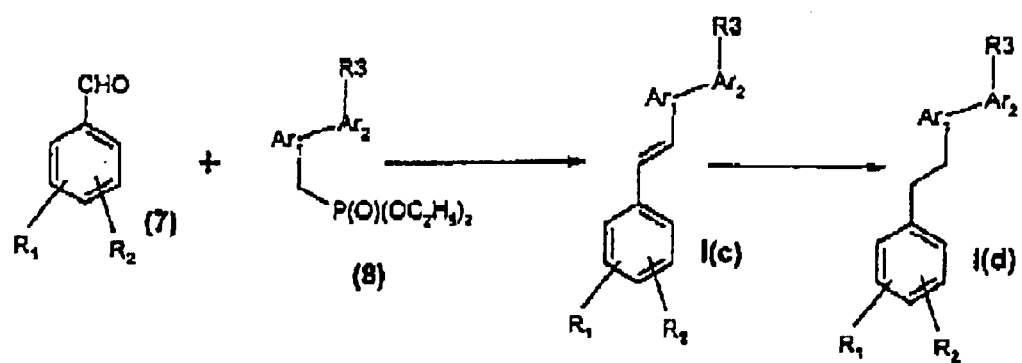

The compounds (1), (2) and (3) can be obtained according to the reaction schemes presented in FIGS. 2, 3 and 4. The methods for preparing the compounds (1) and (2) have the advantage of limiting the number of preparation steps.

In FIG. 2, (a) represents a reaction with $BH_3$ in dioxane, (b) represents a reaction with $CH_3OCH_2Cl$ in the presence of sodium hydride in a dimethylformamide solvent, (c) represents a reaction with n-butyllithium in the presence of $CO_2$ in tetrahydrofuran, (d) represents a reaction with n-butyllithium in tetrahydrofuran followed by a reaction with dimethylformamide, (e) represents a reduction reaction with sodium borohydride in a methanol-tetrahydrofuran solvent and (f) represents a reaction with carbon tetrabromide in the presence of triphenylphosphine in a dichloromethane solvent.

In FIG. 3, (a) represents a reaction with $BH_3$ in dioxane, (b) represents a reaction with methanol in the presence of sulphuric acid, (c) represents a reaction with t-$C_4H_9(CH_3)_2SiCl$ in the presence of imidazole in a dimethylformamide solvent, (d) represents a reaction with $LiAlH_4$ in ether, (e) represents a reaction with benzoyl chloride in the presence of triethylamine in tetrahydrofuran, (f) represents a reaction with $(C_4H_9)_4NF$ in tetrahydrofuran and (g) represents a reaction with carbon tetrabromide in the presence of triphenylphosphine in a dichloromethane solvent.

The derivatives (3) can be obtained according to the reaction scheme indicated in FIG. 4. A Suzuki-type reaction between a boronic derivative (4) and an iodoaryl derivative (5) in the presence of a catalyst such as tetrakis(triphenylphosphine)palladium gives the ester derivative (6) which is converted into the derivative (3) by reaction with an alkylmagnesium or cycloalkylmagnesium halide or an alkyllithium.

The compounds of formula I(c) can be obtained (FIG. 5) by a Horner-Emmons reaction between the phosphonate derivative (8) (obtained from the corresponding benzyl bromide by an Arbuzov reaction) and the benzaldehyde (7).

The compounds of formula I(d) can be obtained from the compounds I(c) by hydrogenation of the double bond in the presence of palladium-on-charcoal.

Figure 6:
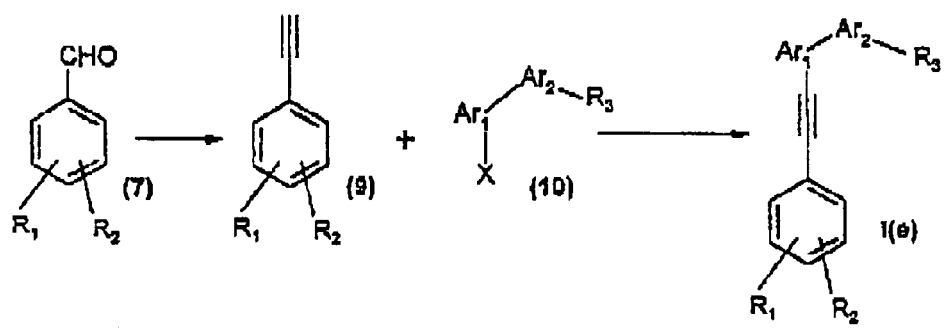

The compounds of formula I(e) can also be obtained (FIG. 6) by a Sonogashira reaction between an acetylenic derivative (9) (obtained by reacting the benzaldehyde (7) by a Corey-Fuchs reaction) and a triflate derivative (X=$OSO_2CF_3$) or iodo derivative (X=I) (10) in the presence of a transition metal catalyst such as $Pd(Cl)_2(PPh_3)_2$ and CuI in a solvent such as triethylamine.

The compounds of general formula (1) have biological properties analogous to those of vitamin D, in particular the properties of transactivation of the vitamin D response elements (VDRE), such as an agonist or antagonist activity with respect to receptors of vitamin D or derivatives thereof. The expression "D vitamins or derivatives thereof" means, for example, the derivatives of vitamin $D_2$ or $D_3$ and in particular 1,25-dihydroxyvitamin $D_3$ (calcitriol).

This agonist activity with respect to receptors of vitamin D or derivatives thereof can be demonstrated "in vitro" by methods known in the field of study of gene transcription (Hansen et al., The Society for Investigative Dermatologie, vol. 1, No. 1, April 1996).

By way of example, the VDR agonist activity can be tested on the HeLa cell line by co-transfection with an expression vector for the human VDR receptor and the reporter plasmid p240Hase-CAT which contains the region −1399 to +76 of rat 24-hydroxylase promoter, cloned upstream of the frame encoding the chloramphenicol-acetyltransferase (CAT)'gene. 18 hours after co-transfection, the test product is added to the medium. 18 hours after treatment, assay of the CAT activity in the cell lysates is carried out by an ELISA test. The results are expressed as percentages of the effect normally observed with $10^{-7}M$ calcitriol.

The agonist activity can also be characterized in this co-transfection system, by determining the dose required to reach 50% of the maximum activity of the product (AC50).

The biological properties of the vitamin D analogues can also be measured by the capacity of the product to inhibit the proliferation of normal human keratinocytes (NHK in culture). The product is added to NHKs cultured under conditions which promote the proliferative state. The product is left in contact with the cells for 5 days. The number of proliferative cells is measured by incorporation of bromodeoxyuridine (BRdU) into the DNA.

The vitamin D receptor agonist activity of the compounds of the invention can also be evaluated "in vivo" by induction of 24-hydroxylase in SKH mice. (Voorhees et al., 1997.108: 513–518).

A subject of the present invention is also, as medicinal product, the compounds of formula (I) as described above.

The compounds according to the invention are particularly suitable in the following fields of treatment:

1) for treating dermatological complaints associated with a keratinization disorder which has a bearing on differentiation and on proliferation, in particular for treating simple acne, comedones, polymorphonuclear leukocytes, rosacea, nodulocystic acne, acne conglobata, senile acne and secondary acne such as solar, medication-related or professional acne, 2) for treating other types of keratinization disorders, in particular ichthyosis, ichthyosiform states, Darier's disease, palmoplantar keratoderma, leukoplasias and leukoplasiform states, and cutaneous or mucous (buccal) lichen, 3) for treating other dermatological complaints with an inflammatory immunoallergic component, with or without cell proliferation disorder, and, in particular, all forms of psoriasis, whether this is cutaneous, mucous or ungual psoriasis, and even psoriatic rheumatism, or alternatively cutaneous atopy, such as eczema or respiratory atopy or alternatively gingival hypertrophy, 4) for treating all dermal or epidermal proliferations, whether benign or malignant and whether they are of viral origin or otherwise, such as common warts, flat warts and verruciform epidermodysplasia, oral or florid papillomatoses, T lymphoma and proliferations which may be induced by ultraviolet radiation, in particular in the case of basocellular and spinocellular epithelioma, as well as any pre-cancerous skin lesion such as keratoacanthomas, 5) for treating other dermatological disorders such as immune dermatitis such as lupus erythematosus, immune bullosis and collagen diseases such as scleroderma, 6) in the treatment of dermatological or general complaints with an immunological component, 7) for combating disorders of sebaceous function such as the hyperseborrhoea of acne or simple seborrhoea, 8) in the treatment of skin disorders due to exposure to UV radiation, as well as for repairing or combating ageing of the skin, whether it is light-induced or chronological ageing, or for reducing actinic keratoses and pigmentations, or any pathologies associated with chronological or actinic ageing, 9) for preventing or treating cicatrization disorders or for preventing or repairing stretchmarks, 10) in the treatment of inflammatory complaints such as arthritis, 11) in the treatment of any complaint of viral origin on the skin or generally, such as Kaposi's syndrome, 12) for treating certain ophthalmological disorders, in particular corneopathies, 13) in the treatment or prevention of cancerous or precancerous states of cancers presenting or possibly being induced by vitamin D receptors, such as, but without limitation, breast cancer, leukaemia, myelodysplasic syndromes and lymphomas, carcinomas of the Malpighian epithelial cells and gastrointestinal cancers, melanomas and osteosarcoma, 14) in the prevention or treatment of alopecia of various origins, in particular alopecia due to chemotherapy or radiation, 15) in the treatment of immune complaints, such as autoimmune diseases, for instance type 1 diabetes mellitus, multiple sclerosis, lupus and lupus-type complaints, asthma, glomerulonephritis, selective dysfunctions of the immune system such as AIDS, or prevention of immune rejection such as kidney, heart, bone marrow, liver, pancreatic islets, pancreas or skin graft rejects, or prevention of graft-versus-host disease, 16) in the treatment of endocrine complaints, given that the vitamin D analogues can modify hormonal secretion such as increasing the secretion of insulin or selectively suppressing the secretion of parathyroid hormone, for example in chronic renal insufficiency and secondary hyperparathyroidism, –p 17) in the treatment of complaints characterized by abnormal management of intracellular calcium, and in the treatment or prevention of pathologies in which calcium metabolism is involved, such as muscular ischaemia (myocardial infarction), –p 18) in the treatment or prevention of vitamin D deficiencies and other mineral homeostasis complaints in plasma and bone, such as rickets, osteomalacia, osteoporosis, in particular in the case of menopausal women, renal osteodystrophy and parathyroid function disorders, 19) in the treatment of complaints of the cardiovascular system such as arteriosclerosis or hypertension; as well as non-insulin-dependent diabetes.

In the therapeutic fields mentioned above, the compounds according to the invention can advantageously be used in combination with retinoids, with corticosteroids or oestrogens, in combination with antioxidants, with α-hydroxy or α-keto acids or derivatives thereof, with potassium-channel blockers, or alternatively in combination with other medicinal products known to interfere with the immune system .(for example cyclosporin, FK 506, glucocorticoids, monoclonal antibodies, cytokines or growth factors, etc.

The term "retinoids" means either natural or synthetic RAR- or RXR-receptor ligands.

The expression "free-radical scavengers" means, for example, α-tocopherol, superoxide dismutase, ubiquinol or certain metal-chelating agents.

The expression "α-hydroxy or α-keto acids or derivatives thereof" means, for example, lactic acid, malic acid, citric acid, glycolic acid, mandelic acid, tartaric acid, glyceric acid, ascorbic acid and salicylic acid derivatives, as well as salts, amides or esters thereof.

The expression "potassium-channel blockers" means, for example, Minoxidil (2,4-diamino-6-piperidinopyrimidine 3-oxide) and derivatives thereof.

A subject of the present invention is also a pharmaceutical composition comprising at least one compound of formula (I) as defined above.

A subject of the present invention is thus also such a pharmaceutical composition intended in particular for treating the abovementioned complaints.

The compounds according to the invention can be administered via the enteral, parenteral, topical or occular route.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. The compounds according to the invention are generally administered at a daily dose of about from 0.001 µg/kg to 1000 µg/kg and preferably of about from 0.01 µg/kg to 100 µg/kg of bodyweight in 1 to 3 dosage intakes.

Via the topical route, the pharmaceutical compositions based on compounds according to the invention are intended for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they are mainly eye drops.

These topical-route or ocular-route compositions contain at least one compound of formula (I) as defined above at a concentration preferably of between 0.0001% and 5% and preferably between 0.001% and 1% relative to the total weight of the composition.

The compounds of formula (I) according to the invention also find an application in the cosmetics field, in particular in body and hair hygiene and especially for treating skin with a tendency towards acne, for regrowth of the hair, for preventing hair loss, for combating the greasy appearance of the skin or the hair, in protecting against the harmful effects of sunlight or in treating physiologically dry skin, for preventing and/or combating light-induced or chronological ageing.

In the cosmetics field, the compounds according to the invention can advantageously be used in combination with retinoids, with corticosteroids, in combination with free-radical scavengers, with α-hydroxy or α-keto acids or derivatives thereof, or alternatively with ion-channel blockers, the various products taken in combination with the compounds of the present invention being as defined above.

The present invention is thus also directed towards a cosmetic composition containing, in a cosmetically acceptable support, at least one compound of formula I as defined above. This cosmetic composition can be in particular in the form of a cream, a milk, a lotion, a gel, microspheres or nanospheres or lipid vesicles or polymer vesicles, a soap or a shampoo.

The concentration of compound of formula I in the cosmetic compositions can be between 0.001% and 3% by weight relative to the total weight of the composition.

The pharmaceutical and cosmetic compositions according to the invention can also contain inert or even pharmacodynamically or cosmetically active additives or combinations of these additives and, in particular: wetting agents; depigmenting agents such as hydroquinone, azelaic acid, caffeic acid or kojic acid; emollients; moisturizing agents such as glycerol, PEG 400, thiamorpholinone and derivatives thereof or urea; antiseborrhoeic or antiacne agents, such as S-carboxymethylcysteine or S-benzylcysteamine and salts and derivatives thereof, or benzoyl peroxide; antibiotics such as erythromycin and esters thereof, neomycin, clindamycin and esters thereof, tetracyclines; antifungal agents such as ketoconazole or poly-4,5-methylene-3-isothiazolinones; agents for promoting regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenylimidazolidine-2,4-dione); non-steroidal anti-inflammatory agents; carotenoids, and in particular β-carotene; anti-psoriatic agents such as anthralin and derivatives thereof, and, finally, eicosa-5,8,11, 14-tetraynoic acid and eicosa-5,8,11-triynoic acid, and esters and amides thereof.

The compositions according to the invention can also contain flavour enhancers, preserving agents such as para-hydroxybenzoic acid esters, stabilizers, moisture regulators, pH regulators, osmotic pressure modifiers, emulsifiers, UV-A and UV-B screening agents, antioxidants such as α-tocopherol, butylhydroxyanisole or butylhydrodxytoluene.

Several examples of the production of active compounds of formula (I) according to the invention, and several concrete formulations based on such compounds, and an example of a test for evaluating the biological activity of compounds of formula (I) according to the invention, will now be given by way of illustration and with no limiting nature.

EXAMPLE 1

{5-[4'(1-Ethyl-1-hydroxypropyl)biphenyl-3-yloxymethyl]-2-hydroxymethylphenyl}methanol a) Dimethyl 4-hydroxymethylphthalate 1,2,4-benzenetricarboxylic anhydride (50 g, 260 mmol) is dissolved in 800 mL of anhydrous dioxane. $BH_3$.THF (260 mmol, 1 eq.) is added dropwise via a dropping funnel, over a period of about 1 h 30 min at room temperature. Stirring is maintained for 12 h and the reaction medium is then poured into a mixture containing 600 mL of saturated ammonium chloride solution and 2 L of dichloromethane. After separation of the phases by settling, the organic phase is dried and the solvents are evaporated off under reduced pressure. The residue obtained is then dissolved in 1 L of methanol and heated to reflux, after addition of 5 mL of sulphuric acid. After reflux for 18 h, the reaction medium is cooled to room temperature and poured directly into a water/ethyl ether mixture (1 L/2 L). After separation of the phases by settling, the aqueous phase is re-extracted with two fractions of ethyl ether (about 700 mL) and the organic phases are then combined, dried and concentrated under reduced pressure. A triester-diester/alcohol mixture is obtained in a yield of 80%, containing 65% of the desired product.

b) Dimethyl 4-(tert-butyldimethylsilanyloxymethyl)-phthalate

The mixture obtained above, containing about 135 mmol of desired product, is dissolved in 400 mL of anhydrous DMF tert-Butyldimethylsilyl chloride (22.5 g, 150 mmol) is then added in a single portion. Next, a total of 13.5 g (195 mmol) of imidazole is added in three portions (slight exothermicity). The reaction medium is stirred for 36 hours and concentrated under reduced pressure. The residue is then dissolved in 500 mL of ethyl ether and then filtered to remove the imidazole hydrochloride formed. The salt is rinsed with 2 fractions of 150 mL of ethyl ether and the organic phases are combined, dried and concentrated under reduced pressure. The residue obtained is then purified by chromatography on a column of silica. The first product collected (eluent: 10 EtOAc/90 heptane) is the desired dimethyl 4-(tert-butyldimethylsilanyloxymethyl)phthalate. 87% yield, overall yield from the starting acid: 45%.

c) [5-(tert-Butyldimethylsilanyloxymethyl)-2-hydroxymethylphenyl]methanol

The diester obtained above (75 g, 220 mmol) is dissolved in 1 L of ethyl ether and cooled to 0° C. under a positive pressure of nitrogen. 4 fractions of 5 g of $LiAlH_4$ (527 mmol) are added cautiously and the mixture is then heated to 50° C. After stirring for 1 h 30 min, the reaction medium is cooled again to 0° C. and then treated successively with 20 mL of water, 20 mL of 15% NaOH and then 60 mL of water. The reaction medium is stirred for 30 minutes until complete disappearance of the grey aluminium salts and their precipitation as white flakes have taken place. The medium is then filtered and, after rinsing the salts with three fractions of ethyl acetate (200 mL), the organic phases are combined, dried and concentrated under reduced pressure. The product obtained represents a yield of 97%.

d) 2-Benzoyloxymethyl-4-(tert-butyldimethylsilanyloxymethyl)benzyl benzoate

The crude diol obtained above (60 g, 212 mmol) is dissolved in 600 mL of anhydrous THF and cooled to 0°C. 74 mL (530 mmol) of triethylamine are then added, followed by 52 mL (448 mmol) of benzoyl chloride. DMAP (500 mg) is then added in a single portion and the mixture is stirred for 30 minutes at 0° C. and then for 12 hours at room temperature. The reaction medium is then filtered to remove the triethylammonium salts precipitated, the salts are rinsed with two fractions of 200 mL of ethyl acetate and the mixture of organic phases is then concentrated under reduced pressure. The residue obtained is taken up in dichloromethane and the organic phase is washed with saturated ammonium chloride solution and then with water. After drying over magnesium sulphate and concentration under reduced pressure, a dark yellow residue is obtained and will be used without further modification for the next step.

e) 2-Benzoyloxymethyl-4-hydroxymethylbenzyl benzoate

The residue obtained above is dissolved in 600 mL of ethyl acetate and 220 mL of tetrabutylammonium fluoride solution (1 M in THF) are added in a single portion. After stirring for 30 minutes at room temperature, the reaction medium is poured into 1 L of saturated ammonium chloride solution. After separation, the aqueous phase is re-extracted with 500 mL of ethyl acetate and the organic phases are combined, dried and evaporated. The product is then purified by chromatography on a column of silica (30 ethyl acetate/70 heptane). A white solid is obtained (m.p.: 91–93° C.).

f) (3,4-bis-Benzoyloxymethyl)benzyl bromide

The above alcohol (65 g, 172 mmol) is dissolved in 350 mL of dichloromethane and $CBr_4$ (67.7 g, 202 mmol) is added. The medium is cooled to 0° C. and a solution of triphenylphosphine (53 9, 202 mmol) in 250 mL of dichloromethane is added dropwise. The reaction medium is then warmed to room temperature and stirred for 2 hours. The medium is then treated with 500 mL of water and extracted with dichloromethane. After drying and concentration of the organic phases, the product is purified by chromatography (eluent: $CH_2Cl_2$/EtOAc) to give a white solid (m.p.: 83° C.) in a yield of 93%.

g) 3-Methoxymethoxyphenylboronic acid 10 g (57.8 mmol) of 3-bromophenol are dissolved in 150 mL of anhydrous DMF. 2.55 g (63.6 mmol) of 60% sodium hydride are then added and the reaction medium is stirred for 1 hour. 4.83 mL (63.6 mmol) of methoxymethyl chloride are then added dropwise and the reaction mixture is stirred for 1 h. After treatment with saturated ammonium chloride solution, extraction with ethyl ether and evaporation of the solvents from the organic phase, the residue obtained is dissolved in 200 mL of anhydrous THF. The mixture is cooled to −78° C. and 25.4 mL (63.6 mmol) of 2.5M butyllithium solution are then added. After stirring for 1 hour at −78° C, 15 mL (65 mmol) of triisopropyl borate are added dropwise. The reaction medium is stirred for 1 hour and then warmed to room temperature, after which it is treated with 1N hydrochloric acid solution. The medium is then extracted with ethyl acetate, after which the organic phases are combined, dried and then concentrated under reduced pressure. After slurrying in heptane and then concentration, a brown solid is obtained (m.p.=45° C., m=5.8 g; Y=67%).

(h) Ethyl 3'-hydroxybiphenyl-4-carboxylate 2 g of 3-methoxymethoxyphenylboronic acid (13.3 mmol) and 1.86 mL (11 mmol) of ethyl 4-iodobenzoate are dissolved in 20 mL of DME. 13.3 mL of 2M potassium carbonate solution (26.6 mmol) are then added and the reaction medium is degassed with a stream of argon for 10 minutes. 640 mg of $Pd(PPh_3)_4$ are then added and the mixture is heated at 90° C. for 14 hours. After treatment with saturated ammonium chloride solution, extraction with ethyl acetate and then drying and evaporation of the solvents from the organic phase, the residue is dissolved in 25 mL of anhydrous methanol and 0.5 mL of sulphuric acid is then added; The reaction medium is refluxed for 15 h and then cooled and finally treated by addition of water. After extraction with ethyl acetate, the organic phase is separated out by settling, dried and then concentrated under reduced pressure. After purification by chromatography on a column of silica, a colourless oil is obtained (m=2 g; Y=75%). ( i) Methyl 3'-[3,4-bis(benzoyloxymethyl)benzyloxy]-biphenyl-4-carboxylate 1 g (4.1 mmol) of ethyl 3'-hydroxybiphenyl-4-carboxylate, 1.98 g (4.5 mmol) of 3,4-bis(benzoyloxymethyl)benzyl bromide and 600 mg of potassium carbonate are dissolved in 40 mL of 2-butanone. The mixture is brought to reflux (80° C.) and then stirred for 4 hours. After cooling, the reaction medium is filtered and then concentrated under reduced pressure. The residue is purified by chromatography on a column of silica, to give a white solid (m.p.=71–72° C.) (m=2.18 g; Y=88%).

j) {5-[4'-(1-Ethyl-1-hydroxypropyl)biphenyl-3-yloxymethyl]-2-hydroxymethylphenyl}methanol 700 mg (1.16 mmol) of ethyl 3'-[3,4-bis(benzoyloxymethyl)benzyloxy]biphenyl-4-carboxylate are dissolved in 30 mL of anhydrous THF and the mixture is then cooled to 0°C. 3.1 mL (9.3 mmol) of ethylmagnesium bromide solution (3M) are then added, after which the reaction medium is warmed to room temperature and stirred for 1 h. After treatment with saturated ammonium chloride solution and then extraction with ethyl acetate, the organic phases are combined, dried and concentrated under reduced pressure. After purification by chromatography on a column of silica, a colourless oil is obtained (m=385 mg, Y=82%).

$^1$H NMR (CDCl$_3$): 0.78 (6H, t, J=7.3Hz), 1.77–1.93 (4H, m), 3.28 (2H, bs), 4.68 (2H, s), 4.69 (2H, s), 5.08 (2H, s), 6.95 (1H, dd), 7.19–7.42 (8H, m), 7.52 (1H, s), 7.55 (1H, s). $^{13}$C (DEPT) 8.3 (2CH$_3$), 35.3 (CH$_2$), 64.2 (CH$_2$), 64.4 (CH$_2$), 70.0 (CH$_2$), 77.8 ($C^{IV}$), 113.7 (CH), 114.1 (CH), 120.3 (CH), 126.4 (2CH), 127.1 (2CH), 127.9 (CH), 129.2 (CH), 130.2 (CH), 130.4 (CH), 137.7 ($C^{IV}$), 139.1 ($C^{IV}$), 139.6 ($C^{IV}$), 140.2 ($C^{IV}$), 142.9 ($C^{IV}$), 145.5 ($C^{IV}$), 159.4 ($C^{IV}$).

EXAMPLE 2

{2-Hydroxymethyl-5-[4'-(1-hydroxy-1-methylethyl)-biphenyl-3-yloxymethyl]phenyl}methanol In a manner similar to that of Example 1(j), by treatment of ethyl 3'[3,4-bis(benzoyloxymethyl)-benzyloxy]biphenyl-4-carboxylate (700 mg, 1.16 mmol) with a methylmagnesium bromide solution (3M), (3.1 mL, 9.3 mmol), a white solid (m.p.=88–90° C.) is obtained after purification by chromatography on a column of silica (m=405 mg, Y=93%).

$^1$H NMR (CDCl$_3$): 1.60 (6H, s), 2.4 (1H, bs), 3.95 (2H, bs), 4.70 (2H, s), 4.71 (2H, s), 5.09 (2H, s), 6.92 (1H, dd, J$_1$=2.5 Hz, J$_2$=7.2 Hz), 7.17–7.19 (2H, m), 7.30–7.38 (3H, m), 7.43 (1H, s), 7.54 (4H, s). $^{13}$C (DEPT) 32.1 (2CH$_3$), 64.1 (CH$_2$), 64.3 (CH$_2$), 70.0 (CH$_2$), 72.7 ($C^{IV}$), 113.8 (CH), 114.1 (CH), 120.3 (CH), 125.3 (2CH), 127.3 (2CH), 127.7 (CH), 129.1 (CH), 130.2 (CH), 130.3 (CH), 137.5 ($C^{IV}$), 139.6 ($C^{IV}$), 139.9 ($C^{IV}$), 140.5 ($C^{IV}$), 142.8 ($C^{IV}$), 149.0 ($C^{IV}$), 159.4 ($C^{IV}$).

EXAMPLE 3

{5-4'-[(1-Ethyl-1-hydroxypropyl)-2'-methylbiphenyl-3-yloxymethyl]-2-hydroxymethylphenyl}methanol (a) Ethyl 3'-hydroxy-2-methylbiphenyl-4-carboxylate In a manner similar to that of Example 1(h), by reaction of 2 g (13.3 mmol) of 3-methoxymethoxyphenylboronic acid with 1.9 9 (8.9 mmol) of 3-methyl-4-bromobenzoic acid, 1.6 g (74%) of the expected product are obtained.

(b) Methyl 3'-[3,4-bis(benzoyloxymethyl)benzyloxy]-2-methylbiphenyl-4-carboxylate In a manner similar to that of Example 1(i) by reaction of 1.6 9 (6.6 mmol) of ethyl 3'-hydroxy-2-methylbiphenyl-4-carboxylate with 3.47 g (7.9 mmol) of 3,4-bis(benzoyloxymethyl)benzyl bromide, 3.7 g (94%) of methyl 3'-[3,4-bis(1-phenylmethanoyloxymethyl)-benzyloxy]-2-methylbiphenyl-4-carboxylate are obtained.

(c) {5-[4'-(1-Ethyl-1-hydroxypropyl)-2'-methylbiphenyl-3-yloxymethyl]-2-hydroxymethylphenyl}methanol In a manner similar to that of Example 1(j), by treatment of methyl 3'-[3,4-bis(benzoyloxymethyl)-benzyloxy]-2-methylbiphenyl-4-carboxylate (800 mg, 1.33 mmol) with an ethylmagnesium bromide solution (3M) (3.6 mL, 10 mmol), a colourless oil is obtained after purification by chromatography on a column of silica (m=475 mg, Y=85%).

$^1$H NMR (CDCl$_3$): 0.81 (6H, t, J=7.5 Hz), 1.74 (1H, s), 1.81–1.94 (4H, m), 2.26 (3H, s), 3.14 (2H, bs), 4.72 (4H, bs), 5.07 (2H, s), 6.91–6.95 (3H, m), 7.18 (2H, s), 7.26 (1H, s), 7.29–7.42 (4H, m). $^{13}$C (DEPT) 8.3 (2CH$_3$), 14.5 (CH$_3$), 35.2 (CH$_2$), 64.3 (CH$_2$), 64.6 (CH$_2$), 69.9 (CH$_2$), 77.7 (C$^{IV}$), 113.6 (CH), 116.2 (CH), 122.6 (CH), 123.3 (CH), 127.8 (CH), 127.9 (CH), 129.2 (CH), 129.5 (CH), 129.7 (CH), 130.4 (CH), 135.1 (C$^{IV}$), 137.8 (C$^{IV}$), 139.5 (C$^{IV}$), 139.9 (C$^{IV}$), 140.1 (C$^{IV}$), 143.8 (C$^{IV}$), 145.3 (C$^{IV}$), 158.7 (C$^{IV}$).

EXAMPLE 4

{2-Hydroxymethyl-5-[4'-(1-hydroxy-1-methylethyl)-2'-methylbiphenyl-3-yloxymethyl]phenyl}methanol In a manner similar Lo that of Example 3(c), by treatment of methyl 3'-[3,4-bis(benzoyloxymethyl)-benzyloxy]-2-methylbiphenyl-4-carboxylate (800 mg, 1.33 mmol) with a methylmagnesium bromide solution (3M) (3.6 mL, 10 mmol), a white solid is obtained (m.p. 45° C.) after purification by chromatography on a column of silica (m=430 mg, Y=83%).

$^1$H NMR (CDCl$_3$): 1.61 (6H, s), 1.82 (1H, s), 2.26 (3H, s), 2.95 (s, 1H), 2.96 (s, 1H), 4.74 (4H, bs), 5.07 (2H, s), 6.91–6.96 (3H, m), 7.18–7.42 (7H, m).

$^{13}$C (DEPT) 21.0 (CH$_3$), 32.2 (2CH$_3$), 64.4 (CH$_2$), 64.6 (CH$_2$), 69.9 (CH$_2$), 72.8 (C$^{IV}$), 113.7 (CH), 116.2 (CH), 122.2 (CH), 122.6 (CH), 126.8 (CH), 127.9 (CH), 129.2 (CH), 129.5 (CH), 130.0 (CH), 130.4 (CH), 135.5 (C$^{IV}$), 137.8 (C$^{IV}$), 139.5 (C$^{IV}$), 140.1 (C$^{IV}$), 140.5 (C$^{IV}$), 143.6 (C$^{IV}$), 148.5 (C$^{IV}$), 158.7 (C$^{IV}$)

EXAMPLE 5

(5-{2-[3'-(1-Ethyl-1-hydroxypropyl)biphenyl-3-yl]ethyl}-2-hydroxymethylphenyl)methanol (a) Ethyl 3'-hydroxybiphenyl-3-carboxylate In a manner similar to that of Example 1(h), by reaction of 2 g (13.3 mmol) of 3-methoxymethoxyphenylboronic acid with 1.83 mL (11 mmol) of ethyl 3-iodobenzoate, 1.9 g (72%) of the expected ethyl ester are obtained.

(b) Ethyl 3'-[3,4-bis(benzoyloxymethyl)benzyloxy]biphenyl-3-carboxylate

In a manner similar to that of Example 1(i), by reaction of 1 g (4.1 mmol) of ethyl 3'-hydroxybiphenyl-3-carboxylate with 1.98 g (4.5 mmol) of 3,4-bis(benzoyloxymethyl)benzyl bromide, 2.1 g (85%) of ethyl 3'-[3,4-bis(benzoyloxymethyl)benzyloxylbiphenyl-3-carboxylate are obtained.

(c) (5-{2-[3'-(1-Ethyl-1-hydroxypropyl)biphenyl-3-yl]ethyl}-2-hydroxymethylphenyl)methanol In a manner similar to that of Example 1(j), by treatment of ethyl 3'-[3,4-bis(benzoyloxymethyl)-benzyloxy]biphenyl-3-carboxylate (400 mg, 0.66 mmol) with an ethylmagnesium bromide solution (3M) (1.8 mL, 5.3 mmol), a colourless oil is obtained after purification by chromatography on a column of silica (m=217 mg, Y=81%).

$^1$H NMR (CDCl$_3$): 0.77 (6H, t, J=7.2 Hz), 1.25 (1H, bs), 1.79–1.88 (4H, m), 3.37 (2H, bs), 4.68 (2H, s), 4.70 (2H, s), 5.11 (2H, s), 6.94 (1H, dd, J$_1$=1.3 Hz, J$_2$=8.3 Hz), 7.18 (2H, s), 7.21–7.42 (8H, m), 7.53 (1H, d, J=1.1 Hz). $^{13}$C (DEPT) 8.3 (2CH$_3$), 35.2 (CH$_2$), 64.2 (CH$_2$), 64.5 (CH$_2$), 70.1 (CH$_2$), 78.0 (C$^{IV}$), 114.1 (CH), 114.4 (CH), 120.4 (CH), 124.8 (CH), 125.1 (CH), 125.5 (CH), 127.8 (CH), 128.8 (CH), 129.0 (CH), 130.2 (CH), 130.4 (CH), 137.8 (C$^{IV}$), 139.6 (C$^{IV}$), 140.2 (C$^{IV}$), 141.0 (C$^{IV}$), 143.4 (C$^{IV}$). 146.7 (C$^{IV}$), 159.3 (C$^{IV}$).

EXAMPLE 6

{2-Hydroxymethyl-5-[3'(1-hydroxy-1-methylethyl)-biphenyl-3-yloxymethyl]phenyl}methanol In a manner similar to that of Example 5(c), by treatment of ethyl 3'-[3,4-bis(benzoyloxymethyl)-benzyloxy]biphenyl-3-carboxylate (380 mg, 0.63 mmol) with a 3.0 M solution of methylmagnesium bromide (1.7 mL,. 5 mmol), a white solid is obtained (m.p. 103–104° C.) after purification by chromatography on a column of silica (m=224 mg, Y=94%).

$^1$H NMR (CDCl$_3$+DMSO): 1.60 (6H, s), 2.96 (1H, bs), 4.29 (1H, t), 4.39 (1H, t), 4.71 (4H, t, J=5.7 Hz), 5.12 (2H, s), 6.94 (1H, dd, J$_1$=2.3 Hz, J$_2$=8.1 Hz), 7.18 (2H, m), 7.29–7.47 (8H, m), 7.69 (1H, s). $^{13}$C (DEPT) 32.2 (2CH$_3$), 63.9 (CH$_2$), 64.1 (CH$_2$), 70.1 (CH$_2$), 72.7 (C$^{IV}$), 114.2 (CH), 114.2 (CH), 120.3 (CH), 123.8 (CH), 124.1 (CH), 125.6 (CH), 127.5 (CH), 128.9 (CH), 129.0 (CH), 130.2 (CH), 130.3 (CH), 137.4 (C$^{IV}$), 140.0 (C$^{IV}$), 140.7 (C$^{IV}$), 141.1 (C$^{IV}$), 143.3 (C$^{IV}$), 150.4 (C$^{IV}$), 159.3 (C$^{IV}$).

EXAMPLE 7

{(5-[4'-(2-Ethyl-2-hydroxybutyl)biphenyl-3-yloxymethyl]-2-hydroxymethylphenyl}methanol (a) Ethyl (3'-hydroxybiphenyl-4-yl)acetate In a manner similar to that of Example 1(h), by reaction of 543 mg (3.6 mmol) of 3-methoxymethoxyphenylboronic acid with 700 mg (2.4 mmol) of ethyl 4-iodophenylacetate, 630 mg (68%) of the expected ethyl ester are obtained.

(b) Ethyl {3'-[3,4-bis(benzoyloxymethyl)benzyloxy]-biphenyl-4-yl}acetate

In a manner similar to that of Example 1(i), by reaction of 360 mg (1.4 mmol) of ethyl (3'-hydroxybiphenyl-4-yl)acetate with 676 mg (1.5 mmol) of 3,4-bis(benzoyloxymethyl)benzyl bromide, 810 mg (94%) of ethyl {3'-[3,4-bis(benzoyloxymethyl)benzyloxy]-biphenyl-4-yl}acetate are obtained.

(c) {{5-[4'-(2-Ethyl-2-hydroxybutyl)biphenyl-3-yloxymethyl]-2-hydroxymethylphenyl}methanol In a manner similar to that of Example 1(j), by treatment of ethyl {3'-[3,4-bis(benzoyloxymethyl)-benzyloxy]

biphenyl-4-yl}acetate (400 mg, 0.66 mmol) with a 3.0M ethylmagnesium bromide solution (1.8 mL, 5.3 mmol), a colourless oil is obtained after purification by chromatography on a column of silica (m=236 mg, Y=85%).

$^1$H NMR (CDCl$_3$): 0.94 (6H, t, J=7.5 Hz), 1.27 (1H, bs), 1.48 (4H, q, J=7.5 Hz), 2.77 (2H, s), 3.17 (2H, bs), 4.71 (4H, s), 5.09 (2H, s), 6.91–6.95 (1H, m), 7.17–7.20 (2H, m), 7.26–7.42 (6H, m), 7.49 (1H, s), 7.52 (1H, m). $^{13}$C (DEPT) 8.4 (2CH$_3$), 30.9 (CH$_2$), 44.8 (CH$_2$), 64.3 (CH$_2$), 64.5 (CH$_2$), 70.0 (CH$_2$), 75.1 (C$^{IV}$), 113.8 (CH), 114.1 (CH), 120.3 (CH), 127.3 (2CH), 127.9 (CH), 129.2 (CH), 130.2 (CH), 130.4 (CH), 131.4 (2CH), 137.3 (C$^{IV}$), 137.7 (C$^{IV}$), 139.3 (C$^{IV}$), 139.6 (C$^{IV}$), 140.2 (C$^{IV}$) 142.9 (C$^{IV}$), 159.4 (C$^{IV}$).

EXAMPLE 8

{5-[3'-(2-Ethyl-2-hydroxybutyl)biphenyl-3-yloxymethyl]-2-hydroxymethylphenyl}methanol (a) Methyl (3'-hydroxybiphenyl-3-yl)acetate In a manner similar to that of Example 1(h), by reaction of 2 g (13.3 mmol) of 3-methoxymethoxyphenylboronic acid with 2 g (9.3 mmol) of 3-bromophenylacetic acid, 1.6 g (72%) of methyl ester are obtained.

(b) Methyl {3-[3,4-bis(benzoyloxymethyl)-benzyloxy]biphenyl-3-yl}acetate

In a manner similar to that of Example 1(i), by reaction of 1 g (4.1 mmol) of methyl (3'-hydroxybiphenyl-3-yl)acetate with 2 g (4.5 mmol) of 3,4-bis(benzoyloxymethyl)benzyl bromide, 2.2 g (91%) of methyl {3'-[3,4-bis(benzoyloxymethyl)benzyloxy]-biphenyl-3-yl}acetate are obtained.

(c) {5-[3'(2-Ethyl-2-hydroxybutyl)biphenyl-3-yloxymethyl]-2-hydroxymethylphenyl}methanol In a manner similar to that of Example 1(j), by treatment of methyl {3'-[3,4-bis(benzoyloxymethyl)-benzyloxy]biphenyl-3-yl}acetate (700 mg, 1.16 mmol) with a 3.0M ethylmagnesium bromide solution (3.1 mL, 9.3 mmol), a colourless oil is obtained after purification by chromatography on a column of silica (m=419 mg, Y=86%).

$^1$H NMR (CDCl$_3$): 0.92 (6H, t, J=7.5 Hz), 1.47 (4H, d, J=7.5 Hz), 2.78 (2H, s), 3.44 (1H, bs), 3.54 (1H, bs), 4.66 (2H, s), 4.67 (2H, s), 5.10 (2H, s), 6.94–6.96 (1H, m), 7.14–7.25 (3H, m), 7.29–7.43 (7H, m). $^{13}$C (DEPT) 8.4 (2CH$_3$), 30.8 (CH$_2$), 45.3 (CH$_2$), 64.2 (CH$_2$), 64.4 (CH$_2$), 70.1 (CH$_2$), 75.2 (C$^{IV}$), 114.1 (CH), 114.3 (CH), 120.4 (CH), 125.6 (CH), 127.7 (CH), 128.9 (CH), 129.0 (CH), 129.7 (CH), 130.2 (CH), 130.2 (CH), 130.4 (CH), 137.8 (C$^{IV}$), 138.3 (C$^{IV}$), 139.6 (C$^{IV}$), 140.3 (C$^{IV}$), 141.2 (C$^{IV}$), 143.0 (C$^{IV}$), 159.3 (C$^{IV}$)

EXAMPLE 9

1-[3'-(3,4-Bis-hydroxymethylbenzyloxy)-biphenyl-3-yl]-2-methylpropan-2-ol

In a manner similar to that of Example 8(c), by treatment of methyl {3'-[3,4-bis(benzoyloxymethyl)-benzyloxy]biphenyl-3-yl}acetate (700 mg, 1.13 mmol) with an ethylmagnesium bromide solution (3M) (3.1 mL, 9.3 mmol), a colourless oil is obtained after purification by chromatography on a column of silica (m=419 mg, Y=92%).

$^1$H NMR (CDCl$_3$): 1.24 (6H, s), 1.65 (114, bs), 2.80 (2H, s), 3.38 (1H, bs), 3.50 (1H, bs), 4.68 (2H, s), 4.09 (2H, s), 5.11 (2H, s), 6.94–6.96 (1H, m), 7.13–7.19 (3H, m), 7.30–7.44 (7H, m). $^{13}$C (DEPT) 29.6 (2CH$_3$), 50.1 (CH$_2$), 64.2 (CH$_2$), 64.4 (CH$_2$), 70.1 (CH$_2$), 71.3 (C$^{IV}$), 114.2 (CH), 114.4 (CH), 120.4 (CH), 125.7 (CH), 127.7 (CH), 128.9 (CH), 129.0 (CH), 129.6 (CH), 130.0 (CH), 130.2 (CH), 130.4 (CH), 137.8 (C$^{IV}$), 138.6 (C$^{IV}$), 139.6 (C$^{IV}$), 140.3 (C$^{IV}$), 141.2 (C$^{IV}$), 142.9 (C$^{IV}$), 159.3 (C$^{IV}$)

EXAMPLE 10

{4-[4'-(1-Ethyl-1-hydroxypropyl)-2'-methylbiphenyl-3-ylsulphanylmethyl]-2-hydroxymethylphenyl}methanol a) Dimethyl 4-(3-bromophenylsulphanylmethyl)phthalate 5 g (26 mmol) of 3-bromothiophenol and 9.2 g (32 mmol) of dimethyl 4-bromomethylphthalate are dissolved in 150 mL of 2-butanone. 4 g (29 mmol) of potassium carbonate are added and the mixture is brought to reflux and stirred for 2 h. The reaction medium is then filtered and concentrated under reduced pressure and the residue is purified by chromatography on a column of silica. A yellow oil (10 g) is obtained in a yield of 100%.

b) [5-(3-Bromophenylsulphanylmethyl)-2-hydroxymethylphenyl]methanol

Dimethyl 4-(3-bromophenylsulphanylmethyl)phthalate (10 g, 26 mmol) is dissolved in 120 mL of anhydrous THF. 2.2 g of lithium borohydride (100 mmol) are then added slowly, after which the reaction medium is refluxed for 12 h. After cooling and treatment with saturated ammonium chloride solution, the reaction medium is extracted with ethyl acetate. The organic phases are combined, dried and concentrated under reduced pressure. The residue is purified by chromatography on a column of silica, to give a colourless oil (7.8 g, Y=89%).

j) [2-Hydroxymethyl-5-(3-tributylstannylphenylsulphanylmethyl)phenyl]methanol 6.2 g (18 mmol) of [5-(3-bromophenylsulphanylmethyl)-2-hydroxymethylphenyl]methanol are dissolved in 120 mL of anhydrous toluene. The mixture is degassed with a stream of argon for 10 minutes, and 18 mL (36 mmol) of hexabutylditin and 416 mg (0.36 mmol) of Pd(PPh$_3$)$_4$ are then added. The reaction medium is then stirred at 120° C. for 48 hours, cooled, treated with saturated ammonium chloride solution and extracted with ethyl acetate. The organic phases are combined, dried and then concentrated under reduced pressure. The residue is purified by chromatography on a column of silica (eluent: pure heptane) to give a yellow oil (m=3.35 g, Y=34%).

k) Methyl 3'-(3,4-bis-hydroxymethyl-benzylsulphanyl)-2-methylbiphenyl-4-carboxylate 1.67 g (3 mmol) of [2-hydroxymethyl-5-(3-tributylstannylphenylsulphanylmethyl)phenyl]methanol are dissolved in 30 mL of toluene and 5 mL of DME. 970 mg (4.5 mmol) of 4-bromo-3-methylbenzoic acid are added and the mixture is degassed with a stream of argon for 10 minutes. Pd(PPh$_3$)$_4$ (175 mg, 0.15 mmol) is then added and the reaction medium is brought to reflux and stirred for 24 h. The reaction medium is then treated with ammonium chloride solution and then extracted with ethyl acetate. The organic phases are combined, dried and then concentrated under reduced pressure. The residue is then dissolved in 50 mL of methanol, 1 mL of sulphuric acid is added and the mixture is then refluxed for 18 h. After cooling and treatment with water, the mixture is extracted with ethyl acetate. The organic phases are combined, dried and then concentrated under reduced pressure. The residue is then purified by chromatography on a column of silica. A colourless oil is obtained (m=180 mg, Y=15%).

f) {4-[4'-(1-Ethyl-1-hydroxypropyl)-2'-methylbiphenyl-3-ylsulphanylmethyl]-2-hydroxymethylphenyl}methanol 130 mg (0.3 mmol) of methyl 3'-(3,4-bis-hydroxymethyl-benzylsulphanyl)-2-methylbiphenyl-4-carboxylate are dissolved in 10 mL of anhydrous THF and 0.7 mL (2 mmol) of an ethylmagnesium bromide solution (3M) are then added. The reaction medium is stirred for 1 h and then treated with ammonium chloride solution. After extraction with ethyl acetate, the organic phases are combined, dried and concentrated under reduced pressure. The residue is purified by chromatography on a column of silica. A colourless oil is obtained (m=105 mg, Y=81%).

$^1$H NMR (DMSO): 0.46 (6H, t, J=6.8 Hz), 1.40–1.60 (4H, m), 1.97 (3H, s), 4.08 (2H, s), 4.39 (2H, s), 4.40 (2H, s), 4.85 (1H, t), 4.90 (1H, t), 6.85–7.23 (10H, m). $^{13}$C (DEPT) 6.3 (2CH$_3$), 18.7 (CH$_3$), 32.8 (2CH$_2$), 34.7 (CH$_2$), 58.4 (CH$_2$), 58.4 (CH$_2$), 73.7 (C$^{IV}$), 121.6 (CH), 124.6 (CH), 124.8 (CH), 125.0 (CH), 125.1 (CH), 125.4 (CH), 125.9 (CH), 126.2 (CH), 126.6 (CH), 126.9 (CH), 131.8 (C$^{IV}$), 133.7 (C$^{IV}$), 134.6 (C$^{IV}$), 136.1 (C$^{IV}$), 136.4 (C$^{IV}$), 137.8 (C$^{IV}$), 140.3 (C$^{IV}$), 144.4 (C$^{IV}$).

EXAMPLE 11

{4-[4'-(1-Ethyl-1-hydroxypropl)-2,2'-dimethylbiphenyl-3-yloxymethyl]-2-hydroxymethylphenyl}methanol a) 3-Bromo-2-methylphenol 20 g (107 mmol) of 3-bromo-2-methylphenylamine are dissolved in 150 mL of aqueous 1.0M sulphuric acid and the mixture is cooled to 0° C. A solution of 8.9 g (129 mmol) of sodium nitrite in 20 mL of water is added slowly. The medium is stirred for 15 minutes at 0° C., and 50 mL of concentrated sulphuric acid are then added. The reaction medium is then heated at 100° C. for 1 hour and then cooled and diluted in water. After extraction with ethyl ether, the residue obtained is recrystallized from a heptane/dichloromethane mixture. A yellow solid is obtained (m.p.=89° C.; m=12.3 g; Y=61%).

b) 1-Bromo-3-methoxymethoxy-2-methylbenzene 13.9 g (74 mmol) of 3-bromo-2-methylphenol are dissolved in 120 mL of dimethylformamide and the mixture is cooled to 0° C. 3.6 g (90 mmol) of 60% sodium hydride are then added portionwise and the medium is stirred for 1 hour. 6.8 mL (90 mmol) of methoxymethyl chloride are then added slowly and the medium is warmed to room temperature and then stirred for 1 hour. After the usual treatment, the residue is purified by chromatography on silica gel (eluent: 80 heptane/20 ethyl acetate). The desired product is obtained in the form of a colourless oil (m=16.2 g; Y=95%).

c) 3-Methoxymethoxy-2-methylbenzene-1-boronic acid 16.2 g (70 mmol) of 1-bromo-3-methoxymethoxy-2-methylbenzene are dissolved in 200 mL of anhydrous THF and the mixture is cooled to −78° C. 33.7 mL (84 mmol) of 2.5M butyllithium are added slowly and the mixture is then maintained at −78° C. for 1 hour. 19.4 mL (84 mmol) of triisopropyl borate are then added dropwise over a period of 15 minutes. The medium is stirred for 30 minutes at the same temperature and then poured into 300 mL of 1N hydrochloric acid. After the usual treatment, the whitish solid residue obtained is rinsed with heptane and then dried under reduced pressure. A flaky white solid is obtained (m=11.8 g; Y=86%).

d) Methyl 3'-hydroxy-2,2'-dimethylbiphenyl-4-carboxylate 1.03 g (5.2 mmol) of 3-methoxymethoxy-2-methylbenzene-1-boronic acid, 1 g (4.4 mmol) of methyl 4-bromo-3-methylbenzoate and 4.4 mL of 2.0M potassium carbonate solution are dissolved in 20 mL of ethylene glycol dimethyl ether. The mixture is degassed using a stream of nitrogen for 10 minutes, and 250 mg (0.22 mmol) of tetrakis(triphenylphosphine)palladium are then added and the medium is stirred for 24 hours at 80° C. After cooling and the usual treatment, the residue obtained is dissolved in 30 mL of methanol and 0.5 mL of sulphuric acid is added. The medium is stirred at room temperature for 6 hours and then poured into an ethyl ether/water mixture. After extraction with ether, the residue is purified by chromatography on silica gel (eluent: 9 heptane/1 ethyl acetate). The desired product is obtained in the form of a thick, colourless oil (m=890 mg; Y=79%).

e) Methyl 3'-[3,4-bis(1-phenylmethanoyloxymethyl)benzyloxy]-2,2'-dimethylbiphenyl-4-carboxylate In a manner similar to that of Example 1(i), by reaction of 515 mg (2 mmol) of methyl 3'-hydroxy-2,2'-dimethylbiphenyl-4-carboxylate with 880 mg (2 mmol) of 3,4-bis(benzoyloxymethyl)benzyl bromide and 300 mg (2.2 mmol) of potassium carbonate, the desired product is obtained in the form of a colourless oil (m=1.22 g; Y=99%).

f) {4-[4'-(1-Ethyl-1-hydroxypropyl)-2,2'-dimethylbiphenyl-3-yloxymethyl]-2-hydroxymethylphenyl}methanol In a manner similar to that of Example 1(j), by reaction of 1.22 g (1.98 mmol) of methyl 3'-[3,4-bis(1-phenylmethanoyloxymethyl)benzyloxy]-2,2'-dimethylbiphenyl-4-carboxylate with 5.3 mL (16 mmol) of 3.0M ethylmagnesium bromide, the desired product is obtained in the form of a white powder (m.p.=81–82° C.; m=360 mg; Y=42%).

$^1$H NMR (CDCl$_3$): 0.82 (t, J=7.4 Hz, 6H); 1.70–1.87 (m, 4H); 1.96 (s, 3H); 2.10 (s, 3H); 4.76 (s, 2H); 4.77 (s, 2H); 5.12 (s, 2H); 6.77 (d, J=7.0 Hz, 1H); 6.88 (d, J=6.9 Hz, 1H); 7.05 (d, J=7.9 Hz, 1H); 7.17 (t, J=7.7 Hz, 2H); 7.26 (s, 1H); 7.37–7.46 (m, 3H).

EXAMPLE 12

{2-Hydroxymethyl-4-[4'-(1-hydroxy-1-propylbutyl)-2,2'-dimethylbiphenyl-3-yloxymethyl]phenyl}methanol a) {2-Hydroxymethyl-4-[4'-(1-hydroxy-1-propylbutyl)-2,2-dimethylbiphenyl-3-yloxymethyl]phenyl}methanol In a manner similar to that of Example 1(j), by reaction of 100 mg (0.25 mmol) of methyl 3'-[3,4-bis(1-phenylmethanoyloxymethyl)benzyloxy]-2,2'-dimethylbiphenyl-4-carboxylate (described in Example 11(e)) with 0.5 mL (1 mmol) of 2.0M ethylmagnesium bromide, the desired product is obtained in the form of a white powder (m.p.=118–120° C.; m=64 mg; Y=56%).

$^1$H NMR (CDCl$_3$) 0.9 (t, J=7.2 Hz, 6H); 1.16–1.36 (m, 4H); 1.73–1.85 (m, 4H); 1.97 (s, 3H); 2.06 (s, 3H); 4.76 (s, 2H); 4.77 (s, 2H); 5.11 (s, 2H); 6.77 (d, J=6.9 Hz, 1H); 6.89 (d, J=6.9 Hz, 1H); 7.04 (d, J=7.9 Hz, 1H); 7.18 (t, J=7.7 Hz, 2H); 7.26 (s, 1H); 7.37–7.46 (m, 3H).

EXAMPLE 13

{4-[4'-(1-Ethyl-1-hydroxypropyl)-2-methylbiphenyl-3-yloxymethyl]-2-hydroxymethylphenyl}methanol a) Methyl 3'-hydroxy-2'-methylbiphenyl-4-carboxylate In a manner similar to that of Example 11(d), by reaction of 3.3 g (16.7 mmol) of 3-methoxymethoxy-2-methylbenzene-1-boronic acid (described in Example 11(c)) with 3 g (13.9 mmol) of ethyl 4-iodobenzoate, 16.7 mL of 2.0M potassium carbonate solution and 800 mg (0.69 mmol) of tetrakis(triphenylphosphine)palladium, followed by deprotection in methanol, the desired product is obtained in the form of a colourless oil (m=3.07 g; Y=77%).

b) Methyl 3'-[3,4-bis(1-phenylmethanoyloxymethyl)benzyloxy]-2'-methylbiphenyl-4-carboxylate In a manner similar to that of Example 1(i), by reaction of 1 g (4.1 mmol) of methyl 3'-hydroxy-2'-methylbiphenyl-4-carboxylate with 2 g (4.5 mmol) of 3,4-bis(benzoyloxymethyl)benzyl bromide and 650 mg (4.7 mmol)

of potassium carbonate, the desired product is obtained in the form of a colourless oil (m=2.4 9; Y=97%).

c) {4-[4'-(1-Ethyl-1-hydroxypropyl)-2-methylbiphenyl-3-yloxymethyl]-2-hydroxymethylphenyl}methanol In a manner similar to that of Example 1(j), by reaction of 2.4 g (4 mmol) of methyl 3'-[3,4-bis(1-phenylmethanoyloxymethyl)benzyloxy]-2'-methylbiphenyl-4-carboxylate with 10.7 mL (32 mmol) of 3.0M ethylmagnesium bromide, the desired product is obtained in the form of a white powder (m.p.=117–118° C.; m=1.1 mg; Y=60%).

$^1$H NMR (DMSO): 0.76 (t, J=7.5 Hz, 6H); 1.70–1.90 (m, 4H); 2.13 (s, 3H); 4.56–4.61 (m, 5H); 5.17 (m, 4H); 6.8 (m, 1H); 7.1 (m, 1H); 7.20–7.30 (m, 3H); 7.40–7.60 (m, 4H).

EXAMPLE 14

{4-[4'-(1-Ethyl-1-hydroxypropyl)-2,2',6'-trimethylbiphenyl-3-yloxymethyl]-2-hydroxymethylphenyl}methanol a) Methyl 3'-hydroxy-2,6,2'-trimethylbiphenyl-4-carboxylate In a manner similar to that of Example 11(d), by reaction of 1.5 g (7.6 mmol) of 3-methoxymethoxy-2-methylbenzene-1-boronic acid (described in Example 11(c)) with 2 g (6.4 mmol) of methyl 3,5-dimethyl-4-trifluoromethanesulphonyloxybenzoate, 7.7 mL of 2.0M potassium carbonate solution and 370 mg (0.32 mmol) of tetrakis(triphenylphosphine)palladium, followed by deprotection in methanol, the desired product is obtained in the form of a white solid (m.p.=149° C.; m=1.34 g; Y=67%).

b) Methyl 3'-[3,4-bis(1-phenylmethanoyloxymethyl)benzyloxy]-2,6,2'-trimethylbiphenyl-4-carboxylate In a manner similar to that of Example 1(i), by reaction of 980 mg (3.6 mmol) of methyl 3'-hydroxy-2,6,2'-trimethylbiphenyl-4-carboxylate with 1.75 g (4.5 mmol) of 3,4-bis(benzoyloxymethyl)benzyl bromide and 570 mg (4.1 mmol) of potassium carbonate, the desired product is obtained in the form of white crystals (m.p.=131–132° C.; m=2.16 g; Y=95%).

c) (4-[4'-(1-Ethyl-1-hydroxypropyl)-2,2',6'-trimethylbiphenyl-3-yloxymethyl]-2-hydroxymethylphenyl}methanol In a manner similar to that of Example 1(j), by reaction of 2.1 g (3.3 mmol) of methyl 3'-[3,4-bis(1-phenylmethanoyloxymethyl)benzyloxy]-2,6,2'-trimethylbiphenyl-4-carboxylate with 8.9 mL (27 mmol) of 3.0M ethylmagnesium bromide, the desired product is obtained in the form of a white powder (m.p.=105–107° C.; m=1.1 mg; Y=73%).

$^1$H NMR (CDCl$_3$): 0.82 (t, J=7.5 Hz, 6H); 1.81–1.85 (m, 4H); 1.87 (s, 3H); 1.95 (s, 6H); 2.25 (bs, 3H); 4.75 (s, 2H); 4.76 (s, 2H); 5.11 (s, 2H); 6.68 (d, J=7.5 Hz, 1H); 6.89 (d, J=7.5 Hz, 1H); 7.1 (s, 2H); 7.15–7.22 (m, 1H); 7.36–7.43 (m, 2H); 7.46 (s, 1H).

EXAMPLE 15

(4-{3-[5-(1-Ethyl-1-hydroxypropyl)-2-pyridyl]phenoxymethyl}-2-hydroxymethylphenyl)methanol a) Ethyl 6-(3-hydroxyphenyl)nicotinate In a manner similar to that of Example 1(h), by reaction of 1 g (6.7 mmol) of 3-methoxymethoxyphenylboronic acid (described in Example 1(g)) and 1.5 g (5.6 mmol) of ethyl 6-iodonicotinate with 5.6 mL of 2.0M potassium carbonate and 320 mg of tetrakis(triphenylphosphine)palladium, followed by deprotection in ethanol, the desired product is obtained in the form of a white solid (m=354 mg; Y=26%).

b) Ethyl 6-{3-[3,4-bis(1-phenylmethanoyloxymethyl)-benzyloxy]phenyl}nicotinate

In a manner similar to that of Example 1(i), by reaction of 277 mg (1.1 mmol) of ethyl 6-(3-hydroxyphenyl)nicotinate with 500 mg (1.1 mmol) of 3,4-bis(benzoyloxymethyl)benzyl bromide and 166 mg (1.2 mmol) of potassium carbonate. The desired product is obtained in the form of white crystals (m.p.=118–120° C.; m=500 mg; Y=73%).

c) (4-{3-[5-(1-Ethyl-1-hydroxypropyl)-2-pyridyl]-phenoxymethyl}-2-hydroxymethylphenyl)methanol In a manner similar to that of Example 1(j), by reaction of 410 mg (0.68 mmol) of ethyl 6-{3-[3,4-bis(1-phenylmethanoyloxymethyl)benzyloxy]phenyl}-nicotinate with 1.8 mL (5.4 mmol) of 3.0M ethylmagnesium bromide, the desired product is obtained in the form of a colourless paste (m=143 mg; Y=51%).

$^1$H NMR (CDCl$_3$): 0.81 (t, J=7.5 Hz, 6H); 1.65 (bs, 1H); 1.73 (bs, 1H); 1.85–1.97 (m, 4H); 2.90 (bs, 3H); 4.74 (s, 2H); 4.76 (s, 2H); 5.15 (s, 2H); 7.01 (d, J=7.6 Hz, 1H); 7.34–7.45 (m, 4H); 7.55 (d, J=7.7 Hz, 1H); 7.67–7.77 (m, 2H); 7.78–7.81 (m, 1H); 8.67 (s, 1H).

EXAMPLE 16

{4-[4'-(1-Ethyl-1-hydroxypropyl)-6,2'-dimethylbiphenyl-3-yloxymethyl]-2-hydroxymethylphenyl}methanol a) 3-Bromo-4-methylphenol In a manner similar to that of Example 11(a), by reaction of 20 g (107 mmol) of 3-bromo-4-methylphenylamine with 8.9 g (129 mmol) of sodium nitrite, a brown oil is obtained, without purification (m=20 g; Y=100%).

b) 2-Bromo-4-methoxymethoxy-1-methylbenzene

In a manner similar to that of Example 11(b), by reaction of 20 g, (107 mmol) of 3-bromo-4-methylphenol with 5.6 g (139 mmol) of 60% sodium hydride and.8.9 mL (139 mmol) of methoxymethyl chloride, the desired product is obtained in the form of an orange-coloured oil (m=12.3 g; Y=50%).

c) 4-Methoxymethoxy-1-methylbenzene-2-boronic acid

In a manner similar to that of Example 11(c), by reaction of 12.3 g (53 mmol) of 2-bromo-4-methoxy-methoxy-1-methylbenzene with 28 mL (69 mmol) of 2.5M butyllithium and 18.4 mL (80 mmol) of triisopropyl borate, a brown oil is obtained (m=10.4 g; Y=99%).

d) Methyl 5'-hydroxy-2,2'-dimethylbiphenyl-4-carboxylate

In a manner similar to that of Example 11(d), by reaction of 3.7 g (18.8 mmol) of 4-methoxymethoxy-1-methylbenzene-2-boronic acid with 3.9 g (17 mmol) of methyl 4-bromo-3-methylbenzoate, 17 mL of 2.0M potassium carbonate solution and 1 mg (0.85 mmol) of tetrakis (triphenylphosphine)palladium, followed by deprotection in methanol, the desired product is obtained in the form of a thick, colourless oil (m=2.87 mg; Y=51%).

e) Methyl 5'-[3,4-bis(1-phenylmethanoyloxymethyl)-benzyloxy]-2,2'-dimethylbiphenyl-4-carboxylate In a manner similar to that of Example 1(i), by reaction of 2.24 g (8.7 mmol) of methyl 5'-hydroxy-2,2'-dimethylbiphenyl-4-carboxylate with 4.20 mg (9.6 mmol) of 3,4-bis(benzoyloxymethyl)benzyl bromide and 1.26 g (9 mmol) of potassium carbonate, the desired product is obtained in the form of a colourless oil (m=5.34 g; Y=99%).

f) {4-[4'-(1-Ethyl-1-hydroxypropyl)-6,2'-dimethyl-biphenyl-3-yloxymethyl]-2-hydroxymethylphenyl}methanol In a manner similar to that of Example 1(j), by reaction of 5.3 g (8.6 mmol) of methyl 5'-[3,4-bis(1-phenylmethanoyloxymethyl)benzyloxy]-2,2'-dimethylbiphenyl-4-carboxylate with 23 mL (69 mmol) of 3.0M ethylmagnesium bromide, the desired product is obtained in the form of a white powder (m=1.68 g; Y=45%).

¹H NMR (DMSO): 0.52 (t, J=7.4 Hz, 6H); 1.51–1.58 (m, 4H); 1.72 (s, 3H); 1.83 (s, 3H); 4.31 (s, 1H), 4.36 (s, 1H); 4.88 (s, 2H); 4.89–4.92 (m, 2H); 6.53 (s, 1H); 6.70–6.74 (dd, $J_1$=2.6 Hz, $J_2$=6.7 Hz, 1H); 6.80 (d, J=7.8 Hz, 1H); 6.99–7.04 (m, 2H); 7.1 (s, 2H); 7.20 (d, 7.3 Hz); 7.28 (s, 1H)

EXAMPLE 17

{4-[4'-(1-Ethyl-1-hydroxypropyl)-6,2',6'-trimethylbiphenyl-3-yloxymethyl]-2-hydroxymethylphenyl}methanol a) Methyl 5'-hydroxy-2,6,2'-trimethylbiphenyl-4-carboxylate In a manner similar to that of Example 11(d), by reaction of 3.7 g (18.8 mmol) of 4-methoxymethoxy-1-methylbenzene-2-boronic acid (described in Example 16(c)) with 5.3 g (17 mmol) of methyl 3,5-dimethyl-4-trifluoromethanesulphonyloxybenzoate, 17 mL of 2.0M potassium carbonate solution and 1 g (0.82 mmol) of tetrakis(triphenylphosphine)palladium, followed by deprotection in methanol, the desired product is obtained in the form of a yellow oil (m=3.0 g; Y=65%).

b) Methyl 5'-[3,4-bis(1-phenylmethancyloxymethyl)-benzyloxy]-2,6,2'-trimethylbiphenyl-4-carboxylate In a manner similar to that of Example 1(i), by reaction of 1.53 g (5.6 mmol) of methyl 5'-hydroxy-2,6,2'-trimethylbiphenyl-4-carboxylate with 2.73 g (6.2 mmol) of 3,4-bis(benzoyloxymethyl)benzyl bromide and 980 mg (5.8 mmol) of potassium carbonate, the desired product is obtained in the form of a yellow oil (m=3.5 g; Y=98%).

c) {4-[4'-(1-Ethyl-1-hydroxypropyl)-6,2',6'-trimethylbiphenyl-3-yloxymethyl]-2-hydroxymethylphenyl}methanol In a manner similar to that of Example 1(j), by reaction of 3.5 g (5.8 mmol) of methyl 5'-[3,4-bis(1-phenylmethanoyloxymethyl)benzyloxy]-2,6,2'-trimethylbiphenyl-4-carboxylate with 15.3 mL (46 mmol) of 3.0M ethylmagnesium bromide, the desired product is obtained in the form of a white powder (m.p.=128° C.; m=1.45 g; Y=56%).

¹H NMR (DMSO): 0.72 (t, J=7.3 Hz, 6H); 1.71–1.75 (m, 4H); 1.83 (s, 3H); 1.92 (s, 6H); 4.31 (s, 1H); 4.45 (s, 1H); 4.55–4.58 (m, 4H); 5.08 (s, 2H); 5.11–5.13 (m, 1H); 6.67 (s, 1H); 6.91–6.95 (dd, $J_1$=2.6 Hz, $J_2$=6.7 Hz, 1H); 7.13 (s, 2H); 7.25 (d, 7.5 Hz, 1H); 7.32 (d, J=7.5 Hz, 1H); 7.42 (d, J=7.5 Hz, 1H); 7.49 (s, 1H).

EXAMPLE 18

{4-[4'-(1-Ethyl-1-hydroxypropyl)-6-methylbiphenyl-3-yloxymethyl]-2-hydroxymethylphenyl}methanol a) Ethyl 5'-hydroxy-2'-methylbiphenyl-4-carboxylate In a manner similar to that of Example 11(d), by reaction of 3.7 g (18.8 mmol) of 4-methoxymethoxy-1-methylbenzene-2-boronic acid described in Example 16(c) with 4.7 g (17 mmol) of ethyl 4-iodobenzoate, 17 mL of 2.0M potassium carbonate solution and 1 g (0.8 mmol) of tetrakis(triphenylphosphine)palladium, followed by deprotection in ethanol, the desired product is obtained in the form of a colourless oil (m=3.07 g; Y=71%).

b) Ethyl 5'-[3,4-bis(1-phenylmethanoyloxymethyl)-benzyloxy]-2'-methylbiphenyl-4-carboxylate In a manner similar to that of Example 1(i), by reaction of 3.07 g (12 mmol) of ethyl 5'-hydroxy-2'-methylbiphenyl-4-carboxylate with 6.7 g (15 mmol) of 3,4-bis(benzoyloxymethyl)benzyl bromide and 2 mg (14 mmol) of potassium carbonate, the desired product is obtained in the form of a colourless oil (m=5.7 g; Y=77%).

c) {4-[4'-(1-Ethyl-1-hydroxypropyl)-6-methylbiphenyl-3-yloxymethyl]-2-hydroxymethylphenyl}methanol In a manner similar to that of Example 1(j), by reaction of 3.8 g (6.2 mmol) of ethyl 5'-[3,4-bis(1-phenylmethanoyloxymethyl)benzyloxy]-2'-methylbiphenyl-4-carboxylate with 16.7 mL (50 mmol) of 3.0M ethylmagnesium bromide, the desired product is obtained in the form of a white powder (m=1.26 mg; Y=48%).

¹H NMR (DMSO): 0.69 (t, J=7.2 Hz, 6H); 1.74–1.77 (m, 4H); 2.15 (s, 3H); 4.52 (s, 1H); 4.54 (s, 1H); 4.56 (s, 1H); 5.05–5.10 (m, 2H); 5.11 (s, 2H); 6.85–6.92 (m, 2H); 7.18 (d, J=8.5 Hz, 1H); 7.25–7.31 (m, 3H); 7.37–7.48 (m, 4H).

EXAMPLE 19

{4-[4'-(1-Ethyl-1-hydroxypropyl)-2',6'-dimethyl-biphenyl-3-yloxymethyl]-2-hydroxyzmethylphenyl}methanol a) Methyl 3'-hydroxy-2,6-dimethylbiphenyl-4-carboxylate In a manner similar to that of Example 1(h), by reaction of 4.48 g (24 mmol) of 3-methoxymethoxyphenylboronic acid (described in Example 1(g)) with 7 g (22.4 mmol) of methyl 3,5-dimethyl-4-trifluoromethanesulphonyloxybenzoate, 24 mL of 2M potassium carbonate and 1.29 g (1.1 mmol) of tetrakis(triphenylphosphine)palladium, followed by deprotection in methanol, the desired product is obtained.

b) Methyl 3'-(3,4-bis(1-phenylmethanoyloxymethyl)-benzyloxy]-2,6-dimethylbiphenyl-4-carboxylate In a manner similar to that of Example 1(i), by reaction of 4.49 g (17.5 mmol) of methyl 3'-hydroxy-2,6-dimethylbiphenyl-4-carboxylate with 8.46 g (19 mmol) of 3,4-bis(benzoyloxymethyl)benzyl bromide and 2.54 g (18 mmol) of potassium carbonate, the desired product is obtained in the form of a yellow oil (m=7.4 g; Y=69%).

c) {4-[4'-(1-Ethyl-1-hydroxypropyl)-2',6'-dimethylbiphenyl-3-yloxymethyl]-2-hydroxymethyl-phenyl}methanol In a manner similar to that of Example 1(j), by reaction of 5.4 g (8.8 mmol) of methyl 3'-[3,4-bis(1-phenylmethanoyloxymethyl)benzyloxy]-2,6-dimethylbiphenyl-4-carboxylate with 23.3 mL (70 mmol) of 3.0M ethylmagnesium bromide, the desired product is obtained in the form of a white powder (m.p.=133° C.; m=2.4 g; Y=65%).

¹H NMR (DMSO): 0.70 (t, J=7.3 Hz, 6H); 1.67–1.75 (m, 4H); 1.98 (s, 6H); 4.48 (s, 1H); 4.54 (s, 1H); 4.56 (s, 1H); 5.11 (s, 2H); 5.14–5.17 (m, 2H); 6.69–6.77 (m, 2H); 7.00 (d, J=8.2 Hz, 1H); 7.1 (s, 2H); 7.30–7.42 (m, 3H); 7.49 (s, 1H).

EXAMPLE 20

1-{4-(3-(3,4-Bis-hydroxymethyl-benzyloxy)phenyl]-2-thiophenyl}-1-propanol a) 1-(4-Bromo-2-thiophenyl)-1-propanol 10 g (52 mmol) of 4-bromothiophene-2-carbaldehyde are dissolved in 200 mL of ethyl ether and 20 mL of THF. 26.6 mL (78 mmol) of 3.0M ethylmagnesium bromide are added slowly. After 2 hours at room temperature, the reaction medium is poured into saturated ammonium chloride solution. After extraction, a yellow oil is obtained (m=11.5 g, Y=99%).

b) 1-(4-Bromo-2-thiophenyl)-1-propanone 11.5 g (52 mmol) of 1-(4-bromo-2-thiophenyl)-1-propanol are dissolved in 300 mL of dichloromethane. 60 g (690 mmol) of manganese dioxide are added and the reaction medium is stirred for 14 hours and then filtered. The desired product is obtained in the form of an orange-coloured oil (m=11.4 g; Y=99%).

c) 1-[4-(3-Hydroxyphenyl)-2-thiophenyl]-1-propanone

In a manner similar to that of Example 1(h), by reaction of 4.6 g (25 mmol) 3-methoxymethoxyphenylboronic acid (described in Example 1(g)) and 5 g (22.8 mmol) of 1-(4-bromo-2-thiophenyl)-1-propanone with 22.8 mL of 2.0M potassium carbonate and 1.32 g of tetrakis(triphenylphosphine)palladium, followed by deprotection in methanol, the desired product is obtained in the form of a white solid (m.p.=112° C.; m=3.87 g: Y=73%).

d) 1-{4-[3-(3,4-Bis(1-phenylmethanoyloxymethyl)-benzyloxy)phenyl]-2-thiophenyl}-1-propanone In a manner similar to that of Example 1(i), by reaction of 3.8 g (16.3 mmol) of 1-[4-(3-hydroxyphenyl)-2-thiophenyl]-1-propanone with 16.9 g (18 mmol) of 3,4-bis(benzoyloxymethyl)benzyl bromide and 2.36 g (17 mmol) of potassium carbonate, the desired product is obtained in the form of white crystals (m.p.=117° C.; m=9.1 g; Y=95%).

e) 1-{4-[3-(3,4-Bis-hydroxymethylbenzyloxy)phenyl]-2-thiophenyl}-1-propanol 4.3 g (7.3 mmol) of 1-{4-[3-(3,4-bis(1-phenylmethanoyloxymethyl)benzyloxy)phenyl]-2-thiophenyl}-1-propanone are dissolved in 10 mL of THF and added dropwise to a suspension of 1.1 g (29 mmol) of lithium aluminium hydride, and the mixture is stirred for 2 hours. After treatment of the reaction medium with 1.1 mL of water, 1.1 mL of 15% sodium hydroxide and 3.3 mL of water, the medium is filtered. After purification by chromatography on silica gel (eluent: 3 heptane/7 ethyl acetate), the desired product is obtained in the form of a colourless oil (m=773 mg; Y=28%).

$^1$H NMR (DMSO): 0.91 (t, J=7.4 Hz, 6H); 1.68–1.77 (m, 2H); 4.53–4.58 (m, 4H); 4.69–4.73 (m, 1H); 5.08–5.14 (m, 1H); 5.16 (s, 2H); 5.58 (d, J=5.4 Hz, 2H); 6.90–6.91 (m, 1H); 7.24–7.43 (m, 6H); 7.52 (s, 1H); 7.73 (s, 1H).

EXAMPLE 21

(4-{3-[4-(1-Ethyl-1-hydroxypropyl)-2-thiophenyl]-phenoxymethyl}-2-hydroxymethylphenyl)methanol a) (4-{3-[4-(1-Ethyl-1-hydroxypropyl)-2-thiophenyl] phenoxymethyl}-2-hydroxymethylphenyl)-methanol In a manner similar to that of Example 1(j), by reaction of 4.3 g (7.3 mmol) of 1-{4-[3-(3,4-bis(1-phenylmethanoyloxymethyl)benzyloxy)phenyl]-2-thiophenyl}-1-propanone (described in Example 20(d)) with 17 mL (51 mmol) of 3.0M ethylmagnesium bromide, the desired product is obtained in the form of a white solid (m.p.=47° C.; m=1.54 g; Y=51%).

$^1$H NMR (DMSO) 0.74 (t, J=7.4 Hz, 6H); 1.68–1.78 (m, 4H); 4.54–4.58 (m, 4H); 4.62 (s, 1H); 5.08–5.13 (m, 1H); 5.16 (s, 2H); 6.92–6.96 (dd, J$_1$=2.6 Hz, J$_2$=6.2 Hz, 1H); 7.19 (d, J=7.5 Hz, 2H): 7.27–7.30 (m, 4H); 7.44 (s, 1H); 7.52 (s, 1H).

EXAMPLE 22

{4-[4'-(1-Ethyl-1-hydroxypropyl)-2'-methylbiphenyl-3-ylmethoxy]-2-hydroxymethylphenyl}methanol a) 1-(4-Bromo-3-methylphenyl)-1-propanone 25 g (116 mmol) of 4-bromo-3-methylbenzoic acid are dissolved in 250 mL of dichloromethane and the mixture is then cooled to 0° C. 10.1 mL (116 mmol) of oxalyl chloride are added slowly, followed by a few drops of dimethylformamide and 16 mL (116 mmol) of triethylamine. After 30 minutes, 12.5 g (128 mmol) of N,O-dimethylhydroxylamine hydrochloride are added slowly, followed by 35.5 mL (255 mmol) of triethylamine. The medium is stirred for 14 hours and then treated with ammonium chloride solution and extracted with dichloromethane. The crude residue is then taken up in ethyl ether and rinsed with 1N sodium hydroxide solution, and then dried and concentrated. The intermediate amide obtained is dissolved in 300 mL of anhydrous THF and cooled to =78° C. 40 mL (120 mmol) of 3.0M ethylmagnesium bromide are added slowly and the reaction medium is warmed to 0° C. and then stirred for 18 hours. After the usual treatment and chromatography on silica gel (9 heptane/1 ethyl acetate), the desired product is obtained in the form of thick colourless oil (m=17 g; Y=64%).

b) 2-(4-Bromo-3-methylphenyl)-2-ethyl-[1,3]dioxolane 16 g (70 mmol) of 1-(4-bromo-3-methylphenyl)-1-propanone are dissolved in 200 mL of toluene. 20 mL (350 mmol) of ethylene glycol and 670 mg (3.5 mmol) of para-toluenesulphonic acid are added. The assembly is equipped with Dean-Stark distillation apparatus and the reaction medium is heated at 130° C. for 16 hours. The medium is cooled and then poured into sodium bicarbonate solution and extracted with ethyl ether. The crude product obtained is in the form of a colourless oil (m=18.6 g; Y=98%).

c) 4'-(2-Ethyl-[1,3]dioxolan-2-yl)-2'-methylbiphenyl-3-carbaldehyde

In a manner similar to that of Example 1(h), by reaction of 6.6 g (44 mmol) of 3-formylbenzeneboronic acid and 10 g (37 mmol) of 2-(4-bromo-3-methylphenyl)-2-ethyl-[1,3] dioxolane with 45 mL of 2.0M potassium carbonate and 2.14 g of tetrakis(triphenylphosphine)palladium, the desired product is obtained in the form of a thick oil (m=9.1 g; Y=84%).

d) [4'-(2-Ethyl-[1,3]dioxolan-2-yl)-2'-methylbiphenyl-3-yl] methanol

In a manner similar to that of Example 20(e), by reaction of 4.5 g (15.2 mmol) of 4'-(2-ethyl-[1,3]dioxolan-2-yl)-2'-methylbiphenyl-3-carbaldehyde with 760 mg (20 mmol) of lithium aluminium hydride, the desired product is obtained in the form of a colourless oil (m=4.4 g, Y=97%).

e) Dimethyl 4-[4'-(2-ethyl-[1,3]dioxolan-2-yl)-2'-methylbiphenyl-3-ylmethoxy]phthalate 4.4 g (14 mmol) of [4'-(2-ethyl-1,3]dioxolan-2-yl)-2'-methylbiphenyl-3-yl]methanol are dissolved in 120 mL of dichloromethane and the mixture is cooled to 0° C. 2.93 mL (16.8 mmol) of diisopropylethylamine are added, followed by slow addition of 1.14 mL (14.7 mmol) of methanesulphonyl chloride. After stirring for 30 minutes, the reaction medium is poured into ammonium chloride solution. After the usual treatment, the residue obtained is dissolved in 150 mL of 2-butanone. 4.2 g (28 mmol) of sodium iodide, 2.13 g (15.4 mmol) of potassium carbonate and 3.23 g (15.4 mmol) of dimethyl 4-hydroxyphthalate are successively added to this solution. The reaction medium is heated at 85° C. for 18 hours and then filtered and concentrated. The residue obtained is purified by chromatography on silica gel (eluent: 8 heptane/2 ethyl acetate). The desired product is obtained in the form of a colourless oil (m=6.89 g, Y=100%).

f) Dimethyl 4-(2'-methyl-4'-propionylbiphenyl-3-ylmethoxy)phthalate 6.8 g (14 mmol) of dimethyl 4-[4'-(2-ethyl-[1,3]dioxolan-2-yl)-2'-methylbiphenyl-3-ylmethoxy]-phthalate are dissolved in 200 mL of methanol and 50 mL of water. 0.5 mL of sulphuric acid is added and the reaction medium is stirred at room temperature for 10 hours. After the usual treatment, the desired product is obtained, without purification, in the form of a colourless oil (m=6.05 g; Y=97%).

g) Dimethyl 4-[4'-(1-ethyl-1-hydroxypropyl)-2'-methylbiphenyl-3-ylmethoxy)phthalate 5 g (11.2 mmol) of dimethyl 4-(2'-methyl-4'-propionylbiphenyl-3-ylmethoxy)phthalate are dissolved in 15 mL of dichloromethane and the mixture is cooled to 0° C. 1.42 mL (11.2 mmol) of trimethylsilyl chloride are added, followed by 13.4 mL (13.4 mmol) of 1.0M dimethylzinc. The medium is stirred for 6 hours and then treated with 10 mL of methanol. 20 mL of 1N hydrochloric acid solution are added and stirring is continued for 1 hour. After extraction with dichloromethane and purification on a column of silica gel (eluent: 6 heptane/4 ethyl acetate), the desired product is obtained in the form of a colourless oil (m=3.25 g; Y=61%).

h) {4-[4'-(1-Ethyl-1-hydroxypropyl)-2'-methylbiphenyl-3-ylmethoxy]-2-hydroxymethylphenyl}methanol In a manner similar to that of Example 20(e), by reaction of 1.5 g (3.15 mmol) of dimethyl 4-[4'(1-ethyl-1-hydroxypropyl)-2'-methylbiphenyl-3-ylmethoxy)-phthalate with 480 mg (12.6 mmol) of lithium aluminium hydride, the desired product is obtained in the form of a white solid (m.p.=87° C.; m=1.03 g; Y=78%).

$^1$H NMR (DMSO): 0.75 (t, J=7.5 Hz, 6H); 1.75–1.79 (m, 4H); 2.27 (s, 3H); 4.47 (d, J=5.2 Hz, 2H); 4.56 (d, J=5.2 Hz, 2H); 4.58 (s, 1H); 4.97 (m, 1H); 5.13 (m, 1H); 5.19 (s, 2H); 6.90–6.91 (m, 1H); 7.12–7.16 (m, 2H); 7.26–7.35 (m, 4H); 7.46 (m, 3H).

EXAMPLE 23

1-[3'-(3,4-Bis-hydroxymethylphenoxymethyl)-2-methylbiphenyl-4-yl]-1-propanol a) 1-[3'-(3,4-Bis-hydroxymethylphenoxymethyl)-2-methylbiphenyl-4-yl]-1-propanol In a manner similar to that of Example 20(e), by reaction of 900 mg (2 mmol) of dimethyl 4-(2'-methyl-4'-propionylbiphenyl-3-ylmethoxy)phthalate (described in Example 22(f)) with 300 mg (8 mmol) of lithium aluminium hydride, the desired product is obtained in the form of a white solid (m.p.=78° C.; m=737 mg; Y=94%).

$^1$H NMR (DMSO): 0.90 (t, J=7.5 Hz, 3H); 1.64–1.68 (m, 2H); 2.26 (s, 3H); 3.39 (m, 1H); 4.46 (s, 1H); 4.47 (d, J=5.2 Hz, 2H); 4.56 (d, J=5.3 Hz, 2H); 4.98 (m, 1H), 5.12–5.16 (m, 1H); 5.19 (s, 1H); 6.90–6.91 (m, 1H); 7.12 (m, 1H); 7.19–7.29 (m, 5H); 7.43–7.49 (m, 3H).

20 EXAMPLE 24

{5-[4'-(1-Ethyl-1-hydroxypropyl)-3'-methylbiphenyl-3-yloxymethyl]-2-hydroxymethylphenyl}methanol a) Methyl 3'-hydroxy-3-methylbiphenyl-4-carboxylate In a manner similar to that of Example 1(h), by reaction of 5.35 g (29 mmol) of 3-methoxymethoxyphenylboronic acid (described in Example 1(g)) and 5.7 g (26.7 mmol) of 4-bromo-2-methylbenzoic acid with 26.7 mL of 2.0M potassium carbonate and 1.54 g of tetrakis(triphenylphosphine) palladium, followed by deprotection in methanol, the desired product is obtained in the form of a colourless oil (m=3.22 g; Y=50%).

b) Methyl 3'-[3,4-bis-(1-phenylmethanoyloxymethyl)benzyloxy]-3-methylbiphenyl-4-carboxylate In a manner similar to that of Example 1(i), by reaction of 1.5 g (6.2 mmol) of methyl 3'-hydroxy-3-methylbiphenyl-4-carboxylate with 3 g (6.88 mmol) of 3,4-bis (benzoyloxymethyl)benzyl bromide and 900 mg (6.4 mmol) of potassium carbonate, the desired product is obtained in the form of a yellow oil (m=3.69 g; Y=99%).

c) {5-[4'-(1-Ethyl-1-hydroxypropyl)-3'-methylbiphenyl-3-yloxymethyl]-2-hydroxymethylphenyl}methanol In a manner similar to that of Example 1(j), by reaction of 4.6 g (7.6 mmol) of methyl 3'-[3,4-bis-(1-phenylmethanoyloxymethyl)benzyloxy]-3-methyl-biphenyl-4-carboxylate with 30.6 mL (61 mmol) of 2.0M ethylmagnesium chloride, the desired product is obtained in the form of a white solid (m.p.=76° C.; m=1.32 g; Y=42%).

$^1$H NMR (DMSO): 0.69 (t, J=7.3 Hz, 6H); 1.68–1.76 (m, 2H); 1.79–2.01 (m, 2H); 2.50 (s, 3H); 4.89 (s, 1H); 4.53–4.57 (m, 4H), 5.07–5.70 (m, 4H); 6.97 (d, J=5 Hz, 1h); 7.21–7.43 (m, 7H); 7.51–7.53 (m, 2H).

EXAMPLE 25

}4-[4'-(1-Ethyl-1-hydroxypropyl)-2'-methylbiphenyl-4-yloxymethyl]-2-hydroxymethylphenyl}methanol a) 4-Methoxymethoxyphenylboronic acid In a manner similar to that of Example 1(g), by reaction of 10 g (57.8 mmol) of 4-bromophenol with 2.55 g (63.6 mmol) of 60% sodium hydride and 4.83 mL (63.6 mmol) of methoxymethyl chloride, followed by 25.4 mL (63.6 mmol) of 2.5M butyllithium solution and 15 mL (65 mmol) of triisopropyl borate, a brown solid is obtained (m.p.=65° C., m=6.2 g; Y=7.3%).

b) Methyl 4'-hydroxy-2-methylbiphenyl-4-carboxylate

In a manner similar to that of Example 1(h), by reaction of 1.61 g (8.7 mmol) of 4-methoxymethoxy-phenylboronic acid and 1.8 g (9.7 mmol) of 4-bromo-3-methylbenzoic acid with 26.7 mL of 2.0M potassium carbonate and 1.54 g of tetrakis(triphenylphosphine)-palladium, followed by deprotection-esterification in methanol, the desired product is obtained in the form of a colourless oil (m=2.06 g; Y=98%).

c) Methyl 4'-[3,4-bis-(1-phenylmethanoyloxymethyl)-benzyloxy]-2-methylbiphenyl-4-carboxylate In a manner similar to that of Example 1(i), by reaction of 2.0 g (8.7 mmol) of methyl 4'-hydroxy-2-methylbiphenyl-4-carboxylate with 4.3 g (9.8 mmol) of 3,4-bis (benzoyloxymethyl)benzyl bromide and 1.29 g (9.3 mmol) of potassium carbonate, the desired product is obtained in the form of a yellow oil (m=4.88 g; Y=91%).

d) {4-[4'(1-Ethyl-1-hydroxypropyl)-2'-methylbiphenyl-4-yloxymethyl]-2-hydroxymethylphenyl}methanol In a manner similar to that of Example 1(j), by reaction of 4.9 g (8 mmol) of methyl 4'-[3,4-bis-(1-phenylmethanoyloxymethyl)benzyloxy]-2-methylbiphenyl-4-carboxylate with 35 mL (70 mmol) of 2.0M ethylmagnesium chloride, the desired product is obtained in the form of a white solid (m.p.=97° C.; m=426 mg; Y=13%).

$^1$H NMR (DMSO): 0.76 (t, J=7.34 Hz, 6H); 1.75–1.84 (m, 4H); 2.31 (s, 3H); 4.56 (s, 1H); 4.60–4.64 (m, 4H); 5.14–5.24 (m, 4H); 7.10–7.18 (m, 3H); 7.25–7.50 (m, 7H); 7.53 (s, 1H)

EXAMPLE 26

}4-[2'-tert-Butyl-4'-(1-ethyl-1-hydroxypropyl) biphenyl-3-yloxymethyl]-2-hydroxymethylphenyl}methanol a) Ethyl 3'-hydroxy-2-tert-butylbiphenyl-4-carboxylate In a manner similar to that of Example 1(h), by reaction of 6.8 g (37 mmol) of 3-methoxymethoxyphenylboronic acid (described in Example 1(g)) with 11 g (31 mmol) of ethyl 3-tert-butyl-4-trifluoromethanesulphonyloxybenzoate, 37 mL of 2M potassium carbonate and 1.8 g of tetrakis (triphenylphosphine)-palladium, followed by deprotection in ethanol, the desired product is obtained in the form of pink crystals (m.p.=118–120° C.; m=5.3 g; Y=57%).

b) Ethyl 3'[3,4-bis-(1-phenylmethanoyloxymethyl) benzyloxy]-2-tert-butylbiphenyl-4-carboxylate In a manner similar to that of Example 1(i), by reaction of 5.3 g (17.7 mmol) of methyl 3'-hydroxy-2-tert-butylbiphenyl-4-carboxylate with 8.46 g (19 mmol) of 3,4-bis(benzoyloxymethyl)benzyl bromide and 2.54 g (18 mmol) of potassium carbonate, the desired product is obtained in the form of a yellow oil (m=11 g; Y=94%).

c) {4-[4'(1-Ethyl-1-hydroxypropyl)-2'-tert-butyl-biphenyl-3-yloxymethyl]-2-hydroxymethylphenyl}methanol In a manner similar to that of Example 1(j), by reaction of 3 g. (4.6 mmol) of methyl 3'[3,4-bis-(1-phenylmethanoyloxymethyl)benzyloxy]-2-tert-butyl-biphenyl-4-carboxylate with 12 mL (36 mmol) of 3.0M ethylmagnesium bromide, the desired product is obtained in the form of a white powder (m.p.=133° C.; m=1.7 g; Y=80%).

$^1$H NMR (CDCl$_3$): 0.83 (t, J=7.4 Hz, 6H); 1.18 (s, 9H) 1.82–1.90 (m, 4H); 2.05 (bs, 3H); 4.74 (s, 4H); 5.07 (s, 2H); 6.88–6.97 (m, 4H); 7.12–7.24 (m, 2H); 7.37 (s, 2H); 7.42 (s, 1H); 7.52 (d, J=1.7 Hz, 1H).

EXAMPLE 27

1-[3'-(3, 4-Bis-hydroxymethylbenzyloxy)-2-methylbiphenyl-4-yl]-2,2-dimethyl-1-propanol a) 4'-Bromo-2'-methylbiphenyl-3-ol In a manner similar to that of Example 1(h), by reaction of 15.3 g (84 mmol) of 3-methoxymethoxyphenylboronic acid (described in Example 1(g)) and 25 g (84 mmol) of 2-bromo-5-iodotoluene with 84 mL of 2.0M potassium carbonate and 4.8 g of tetrakis-(triphenylphosphine) palladium, followed by deprotection in methanol, the desired product is obtained in the form of a colourless oil (m=11.8 g; Y=50%).

b) Dimethyl 4-bromomethylphthalate 36 g (176 mmol) of dimethyl 4-hydroxymethylphthalate are dissolved in 300 mL of dichloromethane and 70 g (211 mmol) of tetrabromomethane are added. A solution of 55.3 g (211 mmol) of triphenylphosphine in 200 mL of dichloromethane is then added slowly and the reaction mixture is stirred for 3 h at room temperature. After treatment with water and extraction with dichloromethane, the residue is purified by chromatography on a column of silica (eluent: dichloromethane). The desired product is obtained in the form of a colourless oil (m=25 g; Y=50%).

c) Dimethyl 4-4'-bromo-2'-methylbiphenyl-3-yloxymethyl) phthalate

In a manner similar to that of Example 1(i), by reaction of 11.8 g (44.8 mmol) of 4'-bromo-2'-methylbiphenyl-3-ol with 14.2 g (49 mmol) of dimethyl 4-bromomethylphthalate and 6.5 g (47 mmol) of potassium carbonate, the desired product is obtained in the form of a yellow oil (m=16.4 g; Y=78%).

d) [4-(4'-Bromo-2'-methylbiphenyl-3-yloxymethyl)-2-hydroxymethylphenyl]methanol 16.4 g (35 mmol) of dimethyl 4-4'-bromo-2'-methylbiphenyl-3-yloxymethyl)phthalate are dissolved in 200 mL of anhydrous THF and 1.5 g (70 mmol) of lithium borohydride are added. The reaction medium is refluxed for 3 h and then cooled and poured onto ice, after which it is diluted with saturated ammonium chloride solution. After extraction, the desired product is obtained in the form of a colourless oil (m=13.3 g; Y=100%).

e) 3'-(3,4-Bis-(tert-butyldimethylsilanyloxymethyl) benzyloxy]-4-bromo-2-methylbiphenyl 13.3 g (34.8 mmol) of [4-(4'-bromo-2'-methylbiphenyl-3-yloxymethyl)-2-hydroxymethylphenyl]methanol are dissolved in 100 mL of DMF. 11.5 g (76 mmol) of tert-butyldimethylchlorosilane and then 6.6 g (97 mmol) of imidazole are added. The medium is stirred for 10 h and then diluted with 400 mL of ethyl ether and filtered. The filtrate is then treated with saturated ammonium chloride solution and rinsed with water. After chromatography on a column of silica gel, the desired product is obtained in the form of a colourless oil (m=20.4 g; Y=91%).

f) 1-{3'-[3,4-Bis-(tert-butyldimethylsilanyloxymethyl) benzyloxy]-2-methylbiphenyl-4-yl}-2,2-dimethyl-1-propanol 2 g (3 mmol) of 3'-[3,4-bis-(tert-butyldimethylsilanyloxymethyl)benzyloxy]-4-bromo-2-methylbiphenyl are dissolved in 30 mL of anhydrous THF and the mixture is cooled to −78° C. 1.4 mL (3.5 mmol) of 2.5 M butyllithium are added slowly and the mixture is maintained at −78° C. for 1 hour. 400 mL (3.7 mmol) of 2,2-dimethylpropionaldehyde are added dropwise and the medium is warmed slowly to room temperature and then treated according to the usual treatment. The desired product is obtained in the form of a colourless oil (m=2 g; Y=100%).

g) 1-[3'-(3,4-Bis-hydroxymethylbenzyloxy)-2-methylbiphenyl-4-yl]-2,2-dimethyl-1-propanol 2 g (3 mmol) of 1-{3'-(3,4-bis-(tert-butyldimethylsilanyloxymethyl)benzyloxy]-2-methylbiphenyl-4-yl}-2,2-dimethyl-1-propanol are dissolved in 20 mL of THF and 7.7 mL (7.7 mmol) of 1 M tetrabutylammonium fluoride are added dropwise. After stirring for 1 hour at room temperature followed by the usual treatment, the residue obtained is purified by chromatography on silica gel. The desired product is obtained in the form of a colourless oil (m=1.15 g; Y=90%).

$^1$H NMR (CDCl$_3$): 0.97 (s, 9H); 2.09 (bs, 2H); 2.25 (s, 3H); 4.40 (s, 1H); 4.75 (s, 2H); 4.76 (s, 2H); 5.09 (s, 2H); 6.91–6.96 (m, 3H); 7.17–7.19 (m, 3H); 7.28–7.44 (m, 4H).

EXAMPLE 28

1-[3'-(3,4-Bis-hydroxymethylbenzyloxy)-2-methyl-biphenyl-4-yl]-2-methyl-1-propanol a) 1-{3'-[3,4-Bis-(tert-butyldimethylsilanyloxymethyl) benzyloxy]-2-methylbiphenyl-4-yl)-2-methyl-1-propanol In a manner similar to that of Example 27(f), by reaction of 2 g (3.1 mmol) of 3'-[3,4-bis-(tert-butyldimethylsilanyloxymethyl)benzyloxy]-4-bromo-2-methylbiphenyl with 1.4 mL (3.5 mmol) of 2.5 M butyllithium and 400 μl (37 mmol) of 2-methylpropionaldehyde, the desired product is obtained in the form of a colourless oil (m=1.1 g; Y=56%).

b) 1-[3'-(3,4-Bis-hydroxymethylbenzyloxy)-2-methylbiphenyl-4-yl]-2-methyl-1-propanol In a manner similar to that of Example 27(g), by reaction of 1.1 g (1.7 mmol) of 1-{3'-[3,4-bis-(tert-butyldimethylsilanyloxymethyl)benzyloxy]-2-methylbiphenyl-4-yl}-2-methyl-1-propanol with 3.8 mL (3.8 mmol) of 1.0M tetrabutylammonium fluoride, the desired product is obtained in the form of a colourless oil (m=460 mg; Y=65%).

$^1$H NMR (CDCl$_3$): 0.85 (d, J=6.7 Hz, 3H); 1.03 (d, J=6.6 Hz, 3H); 1.99 (m, 1H); 2.25 (s, 3H); 4.35 (d, J=6.9 Hz, 1H); 4.73 (s, 2H); 4.74 (s, 2H); 5.08 (s, 2H); 6.92–6.95 (m, 3H); 7.14–7.20 (m, 3H); 7.28–7.43 (m, 4H).

EXAMPLE 29

{2-Hydroxymethyl-4-[methyl (trifluorohydroxytrifluoromethylethyl)biphenyl-3-yloxymethyl]phenyl}methanol.

a) 2-{3'-(3,4-Bis(tert-butyldimethylsilanyloxymethyl)benzyloxy]-2-methylbiphenyl-4-yl}-1,1,1,3,3,3-hexafluoro-2-propanol In a manner similar to that of Example 27(f), by reaction of 4 g (6.2 mmol) of 3'[3,4-bis-(tert-butyldimethylsilanyloxymethyl)benzyloxy]-4-bromo-2-methylbiphenyl with 2.7 mL (6.8 mmol) of 2.5 M butyl-lithium and an excess of hexafluoroacetone, the desired product is obtained in the form of a colourless oil (m=2.35 g; Y=52%).

b) {2-Hydroxymethyl-4-[methyl (trifluorohydroxytrifluoromethylethyl)biphenyl-3-yloxymethyl]phenyl}-methanol In a manner similar to that of Example 27(g), by reaction of 2.3 g (3.2 mmol) of 2-{3'-[3,4-bis(tert-butyldimethylsilanyloxymethyl)benzyloxy]-2-methylbiphenyl-4-yl)-1,1,1,3,3,3-hexafluoro-2-propanol with 7 mL (7 mmol) of 1.0M tetrabutylammonium fluoride, the desired product is obtained in the form of a colourless oil (m=1.2 g; Y=75%).

$^1$H NMR (CDCl$_3$): 2.28 (s, 3H); 2.37 (bs, 2H); 4.74 (s, 4H); 5.08 (s, 2H); 6.91–6.99 (m, 3H); 7.26–7.43 (m, 5H); 7.53–7.59 (m, 3H).

EXAMPLE 30

Formulation Examples

1) Oral Route (a) The composition below is prepared in the form of a 0.2 g tablet:

Compound of Example 1 . . . 0.005 g
Pregelatinized starch . . . 0.065 g
Microcrystalline cellulose . . . 0.075 g
Lactose . . . 0.050 g
Magnesium stearate . . . 0.005 g For the treatment of ichthyosis, 1 to 3 tablets per day are administered to an adult individual for 1 to 12 months depending on the severity of the case treated.

(b) A drinkable suspension, intended to be packaged in 5 ml ampules, is prepared:

Compound of Example 2 . . . 0.050 mg
Glycerol . . . 0.500 g
70% sorbitol . . . 0.500 g
Sodium saccharinate . . . 0.010 g
Methyl para-hydroxybenzoate . . . 0.040 g
Flavouring q.s.
Purified water q.s. . . . 5 ml For the treatment of acne, 1 ampule per day is administered to an adult individual for 1 to 12 months depending on the severity of the case treated.

(c) The formulation below intended to be packaged in gel capsules is prepared:

Compound of Example 4 . . . 0.0001 mg
Corn starch . . . 0.060 g
Lactose q.s. . . . 0.300 g The gel capsules used consist of gelatin, titanium oxide and a preserving agent.

In the treatment of psoriasis, 1 gel capsule per day is administered to an adult individual for 1 to 12 months.

(d) The formulation below intended to be packed in gel capsules is prepared:

Compound of Example 5 . . . 0.02 mg
Cyclosporin . . . 0.050 g
Corn starch . . . 0.060 g
Lactose q.s. . . . 0.300 g The gel capsules used consist of gelatin, titanium oxide and a preserving agent.

In the treatment of psoriasis, 1 gel capsule per day is administered to an adult individual for 1 to 12 months.

2) Topical Route (a) The nonionic water-in-oil cream below is prepared:

Compound of Example 9 . . . 0.100 g
Mixture of emulsifying lanolin
alcohols, waxes and refined oils, sold by the company BDF under the name "Anhydrous eucerin . . . 39.900 g
Methyl para-hydroxybenzoate . . . 0.075 g
Propyl para-hydroxybenzoate . . . 0.075 g
Sterile demineralized water q.s. . . . 100.000 g This cream is applied to skin afflicted with psoriasis 1 to 2 times a day for 1 to 12 months.

(b) A gel is prepared by preparing the formulation below:

Compound of Example 28 . . . 0.001 g
Erythromycin base . . . 4.000 g
Butylhydroxytoluene . . . 0.050 g
Hydroxypropylcellulose sold by the company Hercules under the name "Klucel HF" . . . 2.000 g
Ethanol (at 95°) q.s. . . . 100.00 g This gel is applied to skin afflicted with dermatitis or with acne 1 to 3 times a day for 6 to 12 weeks depending on the severity of the case treated.

(c) An antiseboric lotion is prepared by mixing together the following ingredients:

Compound of Example 12 . . . 0.030 g
Propylene glycol . . . 5.000 g
Butylhydroxytoluene . . . 0.100 g
Ethanol (at 95°) q.s. . . . 100.000 g This lotion is applied twice a day to a seborrhoeic scalp and a significant improvement is observed within a period of 2 to 6 weeks.

(d) A cosmetic composition to combat the harmful effects of sunlight is prepared by mixing together the following ingredients:

Compound of Example 7 . . . 1.000 g
Benzylidenecamphor . . . 4.000 g
Fatty acid triglycerides. . . . 31.000 g
Glyceryl monostearate . . . 6.000 g
Stearic acid . . . 2.000 g
Cetyl alcohol . . . 1.200 g
Lanolin . . . 4.000 g
Preserving agents . . . 0.300 g
Propylene glycol . . . 2.000 g
Triethanolamine . . . 0.500 g
Fragrance . . . 0.400 g
Demineralized water q.s. . . . 100.000 g This composition is applied daily and helps to combat light-induced ageing.

(e) The nonionic oil-in-water cream below is prepared:

Compound of Example 23 . . . 0.500 g
Retinoic acid . . . 0.020 g
Cetyl alcohol . . . 4.000 g
Glyceryl monostearate . . . 2.500 g
PEG-50 stearate . . . 2.500 g Karite butter . . . 9.200 g
Propylene glycol . . . 2.000 g
Methyl para-hydroxybenzoate . . . 0.075 g
Propyl para-hydroxybenzoate . . . 0.075 g
Sterile demineralized water q.s. . . . 100.000 g This cream is applied to skin afflicted with psoriasis 1 to 2 times a day for 30 days for an attacking treatment, and indefinitely for a maintenance treatment.

(f) A topical gel is prepared by mixing together the following ingredients:

Compound of Example 19 . . . 0.050 g
Ethanol . . . 43.000 g
α-Tocopherol . . . 0.050 g
Carboxyvinyl polymer sold under the name "Carbopol 941" by the company "Goodrich" . . . 0.500 g
Triethanolamine as an aqueous solution at 20% by weight . . . 3.800 g
Water . . . 9.300 g
Propylene glycol q.s. . . . 100.000 g This gel is applied in the treatment of acne 1 to 3 times a day for 6 to 12 weeks depending on the severity of the case treated.

(g) A lotion for preventing hair loss and for promoting regrowth of the hair is prepared by mixing together the following ingredients:

Compound of Example 13 . . . 0.05 g
Compound sold under the name "Minoxidil" . . . 1.00 g
Propylene glycol . . . 20.00 g
Ethanol . . . 34.92 g
Polyethylene glycol (molecular mass=400) . . . 40.00 g
Butylhydroxyanisole . . . 0.01 g
Butylhydroxytoluene . . . 0.02 g
Water q.s. . . . 100.00 g This lotion is applied 1 to 2 times a day for 3 months to a scalp which has suffered hair loss, and indefinitely for a maintenance treatment.

(h) An anti-acne cream is prepared by mixing together the following ingredients:

Compound of Example 5 . . . 0.050 g
Retinoic acid . . . 0.010 g
Mixture of glyceryl stearate and polyethylene glycol stearate (75 mol) sold under the name "Gelot 64" by the company "Gattefosse" . . . 15.000 g
Polyoxyethylenated kernel oil containing 6 mol of ethylene oxide, sold under the name "Labrafil M2130 CS" by the company "Gattefosse" . . . 8.000 g
Perhydrosqualene . . . 10.000 g
Preserving agents. . . . q.s.
Polyethylene glycol (molecular mass=400) . . . 8.000 g
Disodium salt of ethylenediamine tetraacetic acid . . . 0.050 g
Purified water q.s. . . . 100.000 g This cream is applied to skin afflicted with dermatitis or acne 1 to 3 times a day for 6 to 12 weeks.

(i) An oil-in-water cream is prepared by preparing the following formulation:

Compound of Example 14 . . . 0.020 g
Betamethasone 17-valerate . . . 0.050 g
S-carboxymethylcysteine . . . 3.000 g
Polyoxyethylene stearate (40 mol of ethylene oxide) sold under the name "Myrj 52" by the company "Atlas" . . . 4.000 g
Sorbitan monolaurate polyoxyethylenated with 20 mol of ethylene oxide, sold under the name "Tween 20" by the company "Atlas" . . . 1.800 g
Mixture of glyceryl mono- and distearate sold under the name "Géléol" by the company "Gattefosse" . . . 4.200 g
Propylene glycol . . . 10.000 g
Butylhydroxyanisole . . . 0.010 g
Butylhydroxytoluene . . . 0.020 g
Cetostearyl alcohol . . . 6.200 g
Preserving agents . . . q.s.
Perhydrosqualene . . . 18.000 g
Mixture of caprylic/capric triglyerides sold under the name "Miglyol 812" by the company "Dynamit Nobel" . . . 4.000 g
Triethanolamine (99% by weight) . . . 2.500 g
Water q.s. . . . 100.000 g This cream is applied twice a day to skin afflicted with inflammatory dermatitis, for 30 days.

(j) The oil-in-water cream below is prepared:

Lactic acid . . . 5.000 g
Compound of Example 8 . . . 0.020 g
Polyoxyethylene stearate (40 mol of ethylene oxide) sold under the name "Myrj 52" by the company "Atlas" . . . 4.000 g
Sorbitan monolaurate polyoxyethylenated with 20 mol of ethylene oxide, sold under the name "Tween 20" by the company "Atlas" . . . 1.800 g
Mixture of glyceryl mono- and distearate sold under the name "Geleol" by the company "Gattefosse" . . . 4.200 g
Propylene glycol . . . 10.000 g
Butylhydroxyanisole . . . 0.010 g
Butylhydroxytoluene . . . 0.020 g
Cetostearyl alcohol . . . 6.200 g
Preserving agents . . . q.s.
Perhydrosqualene . . . 18.000 g
Mixture of caprylic/capric triglyerides sold under the name "Miglyol 812" by the company "Dynamit Nobel" . . . 4.000 g
Water q.s. . . . 100.000 g This cream is applied once a day, and helps to combat ageing, whether light-induced or chronological.

(k) The anhydrous ointment below is prepared:

Compound of Example 25 . . . 5.000 g
Liquid petroleum jelly . . . 50.000 g
Butylhydroxytoluene . . . 0.050 g
White petroleum jelly . . . q.s. 100 g This ointment is applied twice a day for 30 days to skin afflicted with squamous dermatitis.

3) Intralesional Route (a) The following composition is prepared:

Compound of Example 16 . . . 0.002 g
Ethyl oleate . . . q.s. 10 g

In the treatment of malignant melanoma, the composition is injected into an adult individual at a frequency of 1 to 7 times a week for 1 to 12 months.

(b) The following composition is prepared:

Compound of Example 10 . . . 0.050 g

Olive oil . . . q.s. 2 g

In the treatment of basocellular carcinoma, the composition is injected into an adult individual at a frequency of 1 to 7 times a week for 1 to 12 months.

(c) The following composition is prepared:

Compound of Example 6 . . . 0.1 mg

Sesame oil . . . q.s. 2 g

In the treatment of spinocellular carcinoma, the composition is injected into an adult individual at a frequency of 1 to 7 times a week for 1 to 12 months.

(d) The following composition is prepared:

Compound of Example 2 . . . 0.001 mg

Methyl benzoate . . . q.s. 10 g

In the treatment of carcinoma of the colon, the composition is injected into an adult individual at a frequency of 1 to 7 times a week for 1 to 12 months.

4) Intratravenous Route (a) The injectable lipid emulsion below is prepared:

Compound of Example 7 . . . 0.001 mg

Soyabean oil . . . 10.000 g

Egg phospholipid . . . 1.200 g

Glycerol . . . 2.500 g

Water for injection q.s. . . . 100.000 g

In the treatment of psoriasis, the composition is injected into an adult individual at a frequency of 1 to 7 times a week for 1 to 12 months.

(b) The injectable lipid emulsion below is prepared:

Compound of Example 3 . . . 0.010 g

Cotton oil . . . 10.000 g

Soyabean lecithin . . . 0.750 g

Sorbitol . . . 5.000 g

DL, α-tocopherol . . . 0.100 g

Water for injection q.s. . . . 100.000 g

In the treatment of ichthyosis, the composition is injected into an adult individual at a frequency of 1 to 7 times a week for 1 to 12 months.

(c) The injectable lipid emulsion below is prepared:

Compound of Example 21 . . . 0.001 g

Soyabean oil . . . 15.000 g

Acetylated monoglycerides . . . 10.000 g

Pluronic F-108 . . . 1.000 g

Glycerol . . . 2.500 g

Water for injection q.s. . . . 100.000 g

In the treatment of leukaemia, the composition is injected into an adult individual at a frequency of 1 to 7 times a week for 1 to 12 months.

(d) The mixed micellar composition below is prepared:

Compound of Example 29 . . . 0.001 g

Lecithin . . . 16.930 g

Glycocholic acid . . . 8.850 g

Water for injection q.s. . . . 100.000 g

In the treatment of malignant melanoma, the composition is injected into an adult individual at a frequency of 1 to 7 times a week for 1 to 12 months.

(e) The cyclodextrin composition below is prepared:

Compound of Example 11 . . . 0.1 mg

β-Cyclodextrin . . . 0.100 g

Water for injection q.s. . . . 10.000 g

In the treatment of graft rejection, the composition is injected into an adult individual at a frequency of 1 to 7 times a week for 1 to 12 months.

(f) The cyclodextrin composition below is prepared:

Compound of Example 4 . . . 0.010 g

2-Hydroxypropyl-β-cyclodextrin . . . 0.100 g

Water for injection q.s. . . . 10.000 g

In the treatment of cancer of the kidney, the composition is injected into an adult individual at a frequency of 1 to 7 times a week for 1 to 12 months.

EXAMPLE 31

Test Example to Evaluate the Biological Activity of the Compounds of the Invention The VDR agonist activity was tested on the HeLa cell line, by co-transfection of an expression vector of the human VDR receptor and of the reporter plasmid p240Hase-CAT which contains the region −1399 to +76 of the rat 24-hydroxylase promoter, cloned upstream of the coding frame of the chloramphenicol-acetyl-transferase (CAT) gene. 18 hours after co-transfection, the test product is added to the medium. After treatment for 18 hours, the CAT activity of the cell lysates is assayed by an ELISA test. The results are expressed as a percentage of the effect normally observed with $10^{-7}$ M of calcitriol.

The agonist activity was characterized in this co-transfection system by determining the dose required to achieve 50% of the maximum activity of the product (AC50).

| Test compound | AC 50 (nM) |
| --- | --- |
| Example 3 | 470 |
| Example 10 | 2045 |
| Example 11 | 291 |
| Example 16 | 46 |
| Example 17 | 194 |
| Example 18 | 133 |
| Example 22 | 451 |

What is claimed is:

1. Compounds which correspond to the general formula (I) below:

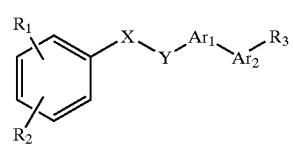

in which:

R$_1$ represents a hydrogen atom, a CH$_3$ radical or a radical —(CH$_2$)$_r$—OR$_4$, R$_2$ represents a radical —(CH$_2$)s—OR$_5$ r, s, R$_4$ and R$_5$ having the meanings given below, X—Y represents a bond selected from the bonds of formulae (a) to (d) below which can be read from left to right or vice-versa:

(a)

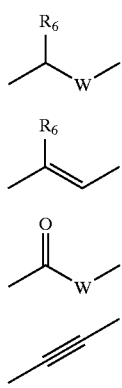

(b)

(c)

R$_6$ and W having the meanings given below,
Ar$_1$ represents a ring of formulae (e) to (i) below:

(d)

(e)

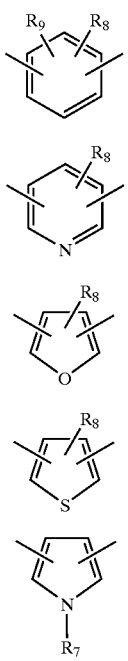

(f)

(g)

(h)

(i)

R$_7$, R$_8$ and R$_9$ having the meanings given below,
Ar$_2$ represents a ring of formulae (j) to (n) below:

(j)

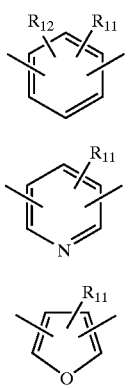

(k)

(l)

-continued (m)

(n)

R$_{10}$, R$_{11}$ and R$_{12}$ having the meanings given below,
R$_3$ represents a radical of formula:

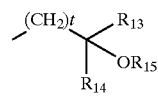

t, R$_{13}$, R$_{14}$ and R$_{15}$ having the meanings given below,
r and s, which may be identical or different, being 1 or 2,
R$_4$ and R$_5$, which may be identical or different, represent a hydrogen atom, an acetyl radical, a benzoyl radical, a trimethylsilyl radical, a tert-butyldimethylsilyl radical or a tetrahydropyranyl radical,
R$_6$ represents a hydrogen atom or a lower alkyl radical,
W represents an oxygen or sulphur atom, a CH$_2$ radical or an NH radical which can be substituted with a lower alkyl radical,
R$_7$ and R$_{10}$, which may be identical or different, represent a hydrogen atom or a lower alkyl radical,
R$_8$, R$_9$, R$_{11}$ and R$_{12}$, which may be identical or different, represent a hydrogen atom, a lower alkyl radical, a halogen atom, a radical —OR$_{16}$, a polyether radical, a CF$_3$ radical, an NO$_2$ radical or an amino radical which may be substituted with one or two lower alkyl radicals,
R$_{16}$ having the meanings given below,
t being 0 or 1,
R$_{13}$ and R$_{14}$, which may be identical or different, represent a hydrogen atom, a lower alkyl radical, a cycloalkyl radical, a CF$_3$ radical or a C$_2$F$_5$ radical,
R$_{15}$ represents a hydrogen atom, an acetyl radical, a trimethylsilyl radical, a tert-butyldimethylsilyl radical or a tetrahydropyranyl radical,
R$_{16}$ represents a hydrogen atom or a lower alkyl radical,
and the optical and geometrical isomers of the said compounds of formula (I), as well as the salts thereof.

2. Compounds according to claim 1, which are in the form of salts of an inorganic or organic acid, in particular hydrochloric acid, sulphuric acid, acetic acid, fumaric acid, hemisuccinic acid, maleic acid or mandelic acid.

3. Compounds according to claim 1, wherein the lower alkyl radicals are selected from the group consisting of methyl, ethyl, isopropyl, tert-butyl and hexyl radicals.

4. Compounds according to claim 1, wherein the cycloalkyl radical corresponds to a cyclopropyl, cyclopentyl or cyclohexyl radical.

5. Compounds according to claim 1, wherein the halogen atom corresponds to a fluorine, chlorine or bromine atom.

6. Compounds according to claim 1, wherein the polyether radical corresponds to a methoxymethoxy, methoxyethoxy or methoxyethoxymethoxy radical.

7. Compounds according to claim 1, which are taken, alone or as mixtures, from the group comprising:

{5-[4'-(1-ethyl-1-hydroxypropyl)biphenyl-3-yloxymethyl]-2-hydroxymethylphenyl}methanol {2-hydroxymethyl-5-[4'-(1-hydroxy-1-methylethyl)biphenyl-3-yloxymethyl]phenyl}methanol {5-[4'-(1-ethyl-1-hydroxypropyl)-2'-methylbiphenyl-3-yloxymethyl]-2-hydroxymethylphenyl}methanol {2-hydroxymethyl-5-[4'-(1-hydroxy-1-methylethyl)-2'-methylbiphenyl-3-yloxymethyl]phenyl}methanol (5-{2-[3'-(1-ethyl-1-hydroxypropyl)biphenyl-3-yl]ethyl}-2-hydroxymethylphenyl)methanol {2-hydroxymethyl-5-[3'-(1-hydroxy-1-methylethyl)-biphenyl-3-yloxymethyl]phenyl}methanol {5-[4'-(2-ethyl-2-hydroxybutyl)biphenyl-3-yloxymethyl]-2-hydroxymethylphenyl}methanol {5-[3'-(2-ethyl-2-hydroxybutyl)biphenyl-3-yloxymethyl]-2-hydroxymethylphenyl}methanol 1-[3'-(3,4-bis-hydroxymethyl-benzyloxy)biphenyl-3-yl]-2-methyl-2-propanol {4-[4'-(1-ethyl-1-hydroxypropyl)-2'-methylbipbenyl-3-ylsulphanylmethyl]-2-hydroxymethylphenyl}methanol {4-[4'-(1-ethyl-1-hydroxypropyl)-2,2'-dimethylbiphenyl-3-yloxymethyl]-2-hydroxymethylphenyl}methanol {2-hydroxymethyl-4-[4'-(1-hydroxy-1-propylbutyl)-2,2'-dimethylbiphenyl-3-yloxymethyl]phenyl}methanol {4-[4'-(1-ethyl-1-hydroxypropyl)-2-methylbiphenyl-3-yloxymethyl]-2-hydroxymethylphenyl}methanol {4-[4'-(1-ethyl-1-hydroxypropyl)-2,2',6'-trimethyl-biphenyl-3-yloxymethyl]-2-hydroxymethylphenyl}methanol (4-{3-[5-(1-ethyl-1-hydroxypropyl)-2-pyridyl]phenoxymethyl}-2-hydroxymethylphenyl}methanol {4-[4'-(1-ethyl-1-hydroxypropyl)-6,2'-dimethylbiphenyl-3-yloxymethyl]-2-hydroxymethylphenyl}methanol {4-[4'-(1-ethyl-1-hydroxypropyl)-6,2',6'-trimethylbiphenyl-3-yloxymethyl]-2-hydroxymethylphenyl}methanol {4-[4'-(1-ethyl-1-hydroxypropyl)-6-methylbiphenyl-3-yloxymethyl]-2-hydroxymethylphenyl}methanol {4-[4'-(1-ethyl-1-hydroxypropyl)-2',6'-dimethylbiphenyl-3-yloxymethyl]-2-hydroxymethylphenyl}methanol 1-{4-[3-(3,4-bis-hydroxymethyl-benzyloxy)phenyl]-2-thienyl}1-propanol(4-{3-[4-(1-ethyl-1-hydroxypropyl)-2-thienyl]phenoxymethyl}-2-hydroxymethylphenyl}methanol {4-[4'-(1-ethyl-1-hydroxypropyl)-2'-methylbiphenyl-3-ylmethoxy]-2-hydroxymethylphenyl}methanol 1-[3'-(3,4-bis-hydroxymethyl-phenoxymethyl)-2-methylbiphenyl-4-yl]-propanol{4-[4'-(1-ethyl-1-hydroxypropyl)-3'-methylbiphenyl-3-yloxymethyl]-2-hydroxymethylphenyl}methanol.

{5-[4'-(1-ethyl-1-hydroxypropyl)-2'-methylbiphenyl-4-yloxymethyl]-2-hydroxymethylphenyl}methanol {4-[2'-tert-butyl-4'-(1-ethyl-1-hydroxypropyl)biphenyl-3-yloxymethyl]-2-hydroxymethylphenyl}methanol 1-[3'-(3,4-bis-hydroxymehyl-benzyloxy)-2-methyl-biphenyl-4-yl]-2,2-dimethyl-1-propanol 1-[3'-(3,4-bis-hydroxymethyl-benzyloxy)-2-methylbiphenyl-4-yl]-2-methyl-1-propanol {2-hydroxymethyl-4[methyl(trifluorohydroxytrifluoromethylethyl)biphenyl-3-yloxymethyl]phenyl}methanol

[5-(2-{5-[4-(1-ethyl-1-hydroxypropyl)-2-methylphenyl]-2-thienyl}ethyl)-2-hydroxymethylphenyl]methanol (5-{5-[4-(1-ethyl-1-hydroxypropyl)-2-methylphenyl]-2-thienylmethoxy}-2-hydroxymethylphenyl)methanol

[5-(2-{5-[2-ethyl-4-(1-ethyl-1-hydroxypropyl)phenyl]-2-thienyl}ethyl)-2-hydroxymethylphenyl]methanol (5-{5-[2-ethyl-4-(1-ethyl-1-hydroxypropyl)phenyl]-2-thienylmethoxy}-2-hydroxymethylphenyl)methanol

[5-(2-{5-[4-(1-ethyl-1-hydroxypropyl)-2-methylphenyl]-4-methyl-2-thienyl}ethyl)-2-hydroxymethylphenyl]methanol (5-{5-[4-(1-ethyl-1-hydroxypropyl)-2-methylphenyl]-4-methyl-2-thienylmethoxy}-2-hydroxymethylphenyl)methanol

[2-hydroxymethyl-5-(2-{5-[methyl(trifluorohydroxytrifluoromethylethyl)phenyl]-2-thienyl}ethyl)phenyl]methanol.

(2-hydroxymethyl-5-{5-[methyl(trifluorohydroxytrifluoromethylethyl)phenyl]-2-thienylmethoxy}phenyl)methanol

[5-(2-{5-[ethyl(trifluorohydroxytrifluoromethylethyl)phenyl]-2-thienyl}ethyl)-2-hydroxymethylphenyl]methanol (5-{5-[ethyl(trifluorohydroxytrifluoromethylethyl)phenyl]-2-thienylmethoxy}-2-hydroxymethylphenyl)methanol

[2-hydroxymethyl-5-(2-{methyl[methyl(trifluorohydroxy-trifluoromethylethyl)phenyl]-2-thienyl}ethyl)phenyl]methanol (2-hydroxymethyl-5-{methyl[methyl(trifluorohydroxy-trifluoromethylethyl)phenyl]-2-thienylmethoxy}phenyl)methanol

[5-(2-{5-[4(1-ethyl-1-hydroxypropyl)-2-methylphenyl]-3-thienyl}ethyl)-2-hydroxymethylphenyl]methanol (5-{5-[4-(1-ethyl-1-hydroxypropyl)-2-methylphenyl]-3-thienylmethoxy}-2-hydroxymethylphenyl)methanol

[5-(2-{5-[2-ethyl-4-(1-ethyl-1-hydroxypropyl)phenyl]-3-thienyl}ethyl)-2-hydroxymethylphenyl]methanol (5-{5-[2-ethyl-4-(1-ethyl-1-hydroxypropyl)phenyl]-3-thienylmethoxy}-2-hydroxymethylphenyl)methanol

[2-hydroxymethyl-5-(2-{5-[methyl(trifluorohydroxytrifluoromethylethyl)phenyl]-3-thienyl}ethyl)phenyl]methanol (2-hydroxymethyl-5-{5-[methyl(trifluorohydroxytrifluoromethylethyl)phenyl]-3-thienylmethoxy}phenyl)-methanol

[5-(2-{5-[ethyl(trifluorohydroxytrifluoromethylethyl)phenyl]-3-thienyl}ethyl)-2-hydroxymethylphenyl]methanol (5-{5-[ethyl(trifluorohydroxytrifluoromethylethyl)phenyl]-3-thienylmethoxy}-2-hydroxymethylphenyl)methanol

[5-(2-{4-[4-(1-ethyl-1-hydroxypropyl)-2-methylphenyl]-2-thienyl}ethyl)-2-hydroxymethylphenyl]methanol (5-{4-[4-(1-ethyl-1-hydroxypropyl)-2-methylphenyl]-2-thienylmethoxy}-2-hydroxymethylphenyl)methanol

[5-(2-{4-[2-ethyl-4-(1-ethyl-1-hydroxypropyl)phenyl]-2-thienyl}ethyl)-2-hydroxymethylphenyl]methanol (5-{4-[2-ethyl-4-(1-ethyl-1-hydroxypropyl)phenyl]-2-thienylmethoxy)-2-hydroxymethylphenyl}methanol

[5-(2-{4-[4-(1-ethyl-1-hydroxypropyl)-2-methylphenyl]-5-methyl-2-thienyl}ethyl)-2-hydroxymethylphenyl]methanol (5-{4-[4-(1-ethyl-1-hydroxypropyl)-2-methylphenyl]-5-methyl-2-thienylmethoxy}-2-hydroxymethylphenyl)methanol

[2-hydroxymethyl-5-(2-{4-[methyl(trifluorohydroxytri-fluoromethylethyl)phenyl]-2-thienyl}ethyl)phenyl]methanol (2-hydroxymethyl-5-{4-[methyl(trifluorohydroxytri-fluoromethylethyl)phenyl]-2-thienylmethoxy}phenyl)methanol

[5-(2-{4-[ethyl(trifluorohydroxytrifluoromethylethyl)-phenyl]-2-thienyl}ethyl)-2-hydroxymethylphenyl]methanol (5-{4-[ethyl(trifluorohydroxytrifluoromethylethyl)-phenyl]-2-thienylmethoxy}-2-hydroxymethylphenyl)methanol

[2-hydroxymethyl-5-(2-{methyl[methyl(trifluorohydroxy-trifluoromethylethyl)phenyl]-2-thienyl}ethyl)phenyl]methanol (2-hydroxymethyl-5-{methyl[methyl(trifluorohydroxytri-fluoromethylethyl)phenyl]-2-thienylmethoxy}phenyl)methanol {5-[2'-ethyl-4'-(1-ethyl-1-hydroxypropyl)-6-methylbiphenyl-3-yloxymethyl]-2-hydroxymethylphenyl}methanol {5-[4'-(1-ethyl-1-hydroxypropyl)-2'-isopropyl-6-methylbiphenyl-3-yloxymethyl]-2-hydroxymethylphenyl}methanol {5-[2'-tert-butyl-4'-(1-ethyl-1-hydroxypropyl)-6-methylbiphenyl-3-yloxymethyl]-2-hydroxymethylphenyl}methanol {5-[ethylmethyl(trifluorohydroxytrifluoromethylethyl)-biphenyl-3-yloxymethyl]-2-hydroxymethylphenyl}methanol {2-hydroxymethyl-5-[2'-isopropyl-6-methyl-4'-(2,2,2-trifluoro-1-'hydroxy-1-trifluoromethylethyl)biphenyl-3-yloxymethyl]phenyl}methanol {5-[dimethylethylmethyl(trifluorohydroxytrifluoro-methylethyl)biphenyl-3-yloxymethyl]-2-hydroxymethyl-phenyl}methanol {5-[6-ethyl-4'-(1-ethyl-1-hydroxypropyl)-2'-methylbi-phenyl-3-yloxymethyl]-2-hydroxymethylphenyl}methanol {5-[4'-(1-ethyl-1-hydroxypropyl)-6-methoxy-2'-methylbi-phenyl-3-yloxymethyl]-2-hydroxymethylphenyl}methanol {5-[6-tert-butyl-4'-(1-ethyl-1-hydroxypropyl)-2'-methylbiphenyl-3-yloxymethyl]-2-hydroxymethylphenyl}methanol {5-[ethylmethyl(trifluorohydroxytrifluoromethylethyl)-biphenyl-3-yloxymethyl]-2-hydroxymethylphenyl}methanol {2-hydroxymethyl-5-[6-methoxy-2'-methyl-4'-(2,2,2-trifluoro-1-hydroxy-1-trifluoromethylethyl)biphenyl-3-yloxymethyl]phenyl}methanol {5-[dimethylethylmethyl(trifluorohydroxytrifluoro-methylethyl)biphenyl-3-yloxymethyl]-2-hydroxymethyl-phenyl}methanol (5-{2-[4'-(1-ethyl-1-hydroxypropyl)-6,2'-dimethyl-biphenyl-3-yl]ethyl}-2-hydroxymethylphenyl)methanol (5-{2-[dimethyl(trifluorohydroxytrifluoromethylethyl)-biphenyl-3-yl]ethyl}-2-hydroxymethylphenyl)methanol (5-{[4'-(11-ethyl-1-hydroxypropyl)-6,2'dimethyl-biphenyl-3-ylamino]methyl}-2-hydroxymethylphenyl)methanol (5-{[dimethyl(trifluorohydroxytrifluoromethylethyl)-biphenyl-3-ylamino]methyl}-2-hydroxymethylphenyl}methanol

[5-({[4'-(1-ethyl-1-hydroxypropyl)-6,2'-dimethylbi-phenyl-3-yl]methylamino}methyl)-2-hydroxymethylphenyl]methanol

[5-({[dimethyl(trifluorohydroxytrifluoromethylethyl)-biphenyl-3-yl]methylamino}methyl)-2-hydroxymethyl-phenyl]methanol.

8. Compounds according to claim 1, which have at least one of the following characteristics:

$R_1$ represents a $CH_3$ or $CH_2OH$ radical, $R_2$ represents a $CH_2OH$ radical, X—Y represents a bond of formula (a) or (c), $R_3$ represents a radical $C(R_{13})(R_{14})OH$.

9. A method for the treatment:

of dermatological complaints associated with a keratinization disorder which has a bearing on differentiation and on proliferation;

of other types of keratinization disorder;

of other dermatological complaints with an inflammatory and/or immunoallergic component, with or without cell proliferation disorders, and all forms of psoriasis, whether it is cutaneous, mucous or ungual psoriasis, and psoriatic rheumatism, or alternatively cutaneous atopy, or alternatively gingival hypertrophy;

of dermal or epidermal proliferations whether benign or malignant and whether they are of viral origin or otherwise, T lymphoma, and proliferations which can be induced by ultraviolet radiation, as well as any pre-cancerous skin lesions such as keratoacanthomas;

of other dermatological disorders comprising immune dermatitis;

of dermatological or general complaints with an immunological component;

of disorders of sebaceous function comprising the hyper-seborrhoea of acne or simple seborrhoea;

of skin disorders due to exposure to UV radiation, of aging of the skin, whether it is light-induced or chronological aging, of pigmentations and actinic keratoses, or any pathologies associated with chronological or actinic aging;

of cicatrization disorders or stretchmarks;

of inflammatory complaints comprising arthritis, or complaints of viral origin on the skin or generally;

of ophthalmological disorders comprising corneopathies;

of cancerous or pre-cancerous states of cancers presenting or possibly being induced by vitamin D receptors, carcinomas of the Malpighian epithelial cells and gastrointestinal cancers, melanomas and osteosarcoma;

of alopecia of various origins;

of immune complaints or of immune rejection;

of endocrine complaints;

of complaints characterized by abnormal management of intracellular calcium, and of pathologies in which calcium metabolism is involved;

of vitamin D deficiencies and other mineral homeostasis complaints in plasma and bone;

of disorders of the cardiovascular system, as well as non-insulin-dependent diabetes comprising administering an effective amount of at least one compound according to claim 1 to a patient in need of such treatment.

10. Pharmaceutical composition, comprising, in a pharmaceutically acceptable support, at least one of the compounds as defined in claim 1.

11. Composition according to claim 10, wherein the concentration of compound(s) according to claim 1 is between 0.0001% and 5% by weight relative to the total weight of the composition.

12. Cosmetic composition comprising, in a cosmetically acceptable support, at least one of the compounds as defined in claim 1.

13. Composition according to claim 12, wherein the concentration of compound is between 0.001% and 3% by weight relative to the total weight of the composition.

14. A method for body or hair hygiene comprising administering an effective amount of at least one compound according to claim 1 to a patient in need thereof.

15. Compounds which correspond to the general formula (I) below:

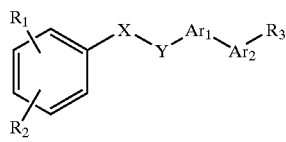
(I)

in which:

$R_1$ represents a hydrogen atom, a $CH_3$ radical or a radical $-(CH_2)r-OR_4$, $R_2$ represents a radical $-(CH_2)s-OR_5$ r, s, $R_4$ and $R_5$ having the meanings given below, X—Y represents a bond selected from the bonds of formulae (a) to (d) below which can be read from left to right or vice-versa:

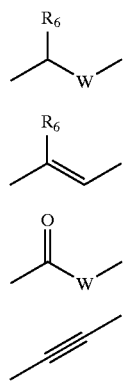

(a)

(b)

(c)

(d)

$R_6$ and W having the meanings given below, $Ar_1$ represents a ring of formulae (e) below:

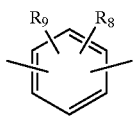
(e)

$R_8$ and $R_9$ having the meanings given below, $Ar_2$ represents a ring of formulae (j) to (n) below:

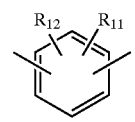
(j)

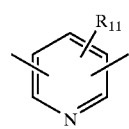
(k)

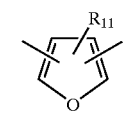
(l)

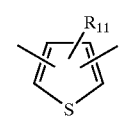
(m)

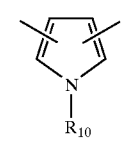
(n)

$R_{10}$, $R_{11}$, and $R_{12}$ having the meanings given below, $R_3$ represents a radical of formula:

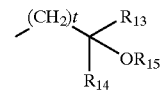

t, $R_{13}$, $R_{14}$ and $R_{15}$ having the meanings given below, r and s, which may be identical or different, being 1 or 2, $R_4$ and $R_5$, which may be identical or different, represent a hydrogen atom, an acetyl radical, a benzoyl radical, a trimethylsilyl radical, a tert-butyldimethylsilyl radical or a tetrahydropyranyl radical, $R_6$ represents a hydrogen atom or a lower alkyl radical, W represents an oxygen or sulphur atom, a $CH_2$ radical or an NH radical which can be substituted with a lower alkyl radical, $R_7$ and $R_{10}$, which may be identical or different, represent a hydrogen atom or a lower alkyl radical, $R_8$, $R_9$, $R_{11}$, and $R_{12}$, which may be identical or different, represent a hydrogen atom, a lower alkyl radical, a halogen atom, a radical $-OR_{16}$, a polyether radical, a $CF_3$ radical, an $NO_2$ radical or an amino radical which may be substituted with one or two lower alkyl radicals, $R_{16}$ having the meanings given below, t being 0 or 1, $R_{13}$ and $R_{14}$, which may be identical or different, represent a hydrogen atom, a lower alkyl radical, a cycloalkyl radical, a $CF_3$ radical or a $C_2F_5$ radical, $R_{15}$ represents a hydrogen atom, an acetyl radical, a trimethylsilyl radical, a tert-butyldimethylsilyl radical or a tetrahydropyranyl radical, $R_{16}$ represents a hydrogen atom or a lower alkyl radical, and the optical and geometrical isomers of the said compounds of formula (I), as well as the salts thereof.

16. The compound of claim 1, wherein said compound is {4-[4'-(1-Ethyl-1-hydroxypropyl)-6,2'-dimethylbiphenyl-3-yloxymethyl]-2-hydroxymethylphenyl}methanol.

* * * * *